US008021998B2

(12) United States Patent
Qin et al.

(10) Patent No.: US 8,021,998 B2
(45) Date of Patent: Sep. 20, 2011

(54) ABSORBENT STRUCTURE WITH SUPERABSORBENT MATERIAL

(75) Inventors: Jian Qin, Appleton, WI (US); Sandra Marie Rogers, Appleton, WI (US); Michael John Niemeyer, Appleton, WI (US); Kenneth Raymond Schueler, Jr., Appleton, WI (US); Steven Michael Hurley, Neenah, WI (US); Lawrence Howell Sawyer, Neenah, WI (US); Whei-Neen Hsu, Greensboro, NC (US); Mark C. Joy, Greensboro, NC (US); Scott J. Smith, Greensboro, NC (US); Markus Frank, Baden-Baden (DE); Nancy Birbiglia Lange, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 12/787,914

(22) Filed: May 26, 2010

(65) Prior Publication Data

US 2010/0261812 A1 Oct. 14, 2010

Related U.S. Application Data

(63) Continuation of application No. 11/153,190, filed on Jun. 15, 2005, now abandoned, which is a continuation of application No. 10/423,709, filed on Apr. 25, 2003, now abandoned.

(51) Int. Cl.
*D04H 1/00* (2006.01)
*D02G 3/00* (2006.01)

(52) U.S. Cl. ........................................ 442/414; 428/365

(58) Field of Classification Search .................. 442/414; 428/365
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,340,563 A | 7/1982 | Appel et al. | |
| 4,587,308 A | 5/1986 | Makita et al. | |
| 4,777,073 A | 10/1988 | Sheth | |
| 4,795,668 A | 1/1989 | Krueger et al. | |
| 5,032,628 A | 7/1991 | Choi et al. | |
| 5,108,820 A | 4/1992 | Kaneko et al. | |
| 5,149,335 A * | 9/1992 | Kellenberger et al. | ........ 604/372 |
| 5,336,552 A | 8/1994 | Strack et al. | |
| 5,382,400 A | 1/1995 | Pike et al. | |
| 5,409,771 A | 4/1995 | Dahmen et al. | |
| 5,462,972 A | 10/1995 | Smith et al. | |
| 5,509,915 A | 4/1996 | Hanson et al. | |
| 5,540,992 A | 7/1996 | Marcher et al. | |
| 5,610,220 A | 3/1997 | Klimmek et al. | |
| 5,669,894 A | 9/1997 | Goldman et al. | |
| 5,672,633 A | 9/1997 | Brehm et al. | |
| 5,676,660 A | 10/1997 | Mukaida et al. | |
| 5,744,564 A | 4/1998 | Stanley, Jr. et al. | |
| 5,836,929 A | 11/1998 | Bewick-Sonntag et al. | |
| 5,994,440 A | 11/1999 | Staples et al. | |
| 6,090,875 A | 7/2000 | Staples et al. | |
| 6,124,391 A | 9/2000 | Sun et al. | |
| 6,239,230 B1 | 5/2001 | Eckert et al. | |
| 6,376,011 B1 | 4/2002 | Reeves et al. | |
| 6,376,618 B1 | 4/2002 | Mitchell et al. | |
| 6,387,495 B1 | 5/2002 | Reeves et al. | |
| 6,388,000 B1 | 5/2002 | Irie et al. | |
| 6,391,451 B1 | 5/2002 | Mitchell et al. | |
| 6,605,673 B1 | 8/2003 | Mertens et al. | |
| 2002/0045869 A1 | 4/2002 | Dodge, II et al. | |
| 2002/0115971 A1 | 8/2002 | Holmes et al. | |
| 2002/0150761 A1 | 10/2002 | Lange et al. | |
| 2002/0156441 A1 | 10/2002 | Sawyer et al. | |
| 2002/0161132 A1 | 10/2002 | Yoshio et al. | |
| 2003/0014027 A1 | 1/2003 | Beihoffer et al. | |
| 2004/0092658 A1 | 5/2004 | Qin et al. | |

FOREIGN PATENT DOCUMENTS

| | | | |
|---|---|---|---|
| EP | 0339461 A1 * | 4/1989 | |
| EP | 0339461 A | 11/1989 | |
| EP | 0640330 B1 | 5/2000 | |
| EP | 1153656 A2 | 11/2001 | |
| JP | 2002302513 | 10/2002 | |
| JP | 2002539281 | 11/2002 | |
| WO | 95/11932 A1 | 5/1995 | |
| WO | WO95/11932 * | 5/1995 | |
| WO | 00/50096 A1 | 8/2000 | |
| WO | 0062730 A1 | 10/2000 | |
| WO | 0062825 A2 | 10/2000 | |
| WO | 0062826 A1 | 10/2000 | |

(Continued)

OTHER PUBLICATIONS

Translation of Notice of Reasons for Rejection regarding Japanese Patent Application No. 2006-510111, dated Aug. 3, 2009.
Mar. 2, 2011 Letter from Associate regarding Notice of Preliminary Rejection for Korean Patent Application No. 10-2005-7019221.
Notice of Written Hearing issued in JP2006-510111 on Feb. 8, 2011.

*Primary Examiner* — Norca L Torres Velazquez
(74) *Attorney, Agent, or Firm* — Armstrong Teasdale LLP

(57) ABSTRACT

An absorbent structure made at least in part from a superabsorbent material having a retention capacity (CRC) as determined by a Centrifuge Retention Capacity Test of at least about 25 g/g and a free swell gel bed permeability (GBP) as determined by a Free Swell Gel Bed Permeability Test of at least $575 \times 10^{-9}$ cm$^2$. In another embodiment, the absorbent structure is made at least in part from a superabsorbent material having a retention capacity (CRC) as determined by a Centrifuge Retention Capacity Test of at least about 25 g/g, an absorbency under load (AUL) at 0.9 psi as determined by an Absorbency Under Load Test of at least 18 and a free swell gel bed permeability (GBP) as determined by a Free Swell Gel Bed Permeability Test of at least about $350 \times 10^{-9}$ cm$^2$.

20 Claims, 5 Drawing Sheets

FOREIGN PATENT DOCUMENTS

| | | |
|---|---|---|
| WO | 0062922 A1 | 10/2000 |
| WO | 0063487 A1 | 10/2000 |
| WO | 01/13841 A1 | 3/2001 |
| WO | 0189591 A2 | 11/2001 |
| WO | 0189592 A2 | 11/2001 |
| WO | 0249565 A2 | 6/2002 |
| WO | 02056812 A2 | 7/2002 |
| WO | 03003808 A2 | 1/2003 |

* cited by examiner

ABSORBENT STRUCTURE WITH SUPERABSORBENT MATERIAL

CROSS-REFERENCE TO RELATED APPLICATION

This application is a continuation of U.S. patent application Ser. No. 11/153,190 filed Jun. 15, 2005, which is a continuation of U.S. patent application Ser. No. 10/423,709, filed Apr. 25, 2003. The entire texts of the above-referenced applications are hereby incorporated by reference.

BACKGROUND OF THE INVENTION

This invention relates generally to absorbent structures used in disposable articles such as diapers, children's training pants, feminine care articles, incontinence articles, bandages, surgical gowns, absorbent wipes and the like, and more particularly to such absorbent structures containing a superabsorbent material having enhanced liquid handling characteristics such as an enhanced combination of retention capacity, free swell gel bed permeability and/or absorbency under load value.

Conventional disposable articles typically include an absorbent structure, also sometimes referred to as an absorbent core or absorbent composite, formed by air-forming, air-laying or other known forming technique. For example, the manufacture of such an absorbent structure may begin by fiberizing a fibrous sheet of hydrophilic material in a fiberizer or other shredding or comminuting device to form discrete fibers. In addition, particles or fibers of superabsorbent material, which are water insoluble, water swellable and capable of absorbing at least about ten times their weight in 0.9 weight percent sodium chloride solution in distilled water (saline solution), are mixed with the discrete fibers. The hydrophilic fibers and superabsorbent material are then entrained in an air stream and directed to a foraminous forming surface upon which the fibers and superabsorbent material are deposited and accumulated to form the absorbent structure.

There is a continuing effort by absorbent structure manufacturers to improve the liquid intake performance of absorbent structures to thereby reduce the tendency of such a structure to leak as it becomes increasingly saturated during use, particularly where the structure is subjected to repeated liquid insults before being discarded. For example, one means of reducing the leakage of absorbent structures has been the extensive use of superabsorbent materials. In addition to increasing the amount of superabsorbent mass, recent efforts in commercial absorbent structure design have generally focused on using a higher concentration of superabsorbent material and less fiber to make the absorbent structure thinner and denser.

However, notwithstanding the increase in total absorbent capacity obtained by increasing the concentration of superabsorbent material, such absorbent structures may still leak during use. The leakage may be in part the result of the structure having an insufficient intake rate, e.g., the rate at which a liquid insult can be taken into and entrained within the structure for subsequent absorption by the superabsorbent material. More particularly, the intake rate of such absorbent structures may decrease upon repeated insults thereof due to the tendency of the superabsorbent material within the structure to swell as it absorbs and thus restrict or otherwise block the open channels between superabsorbent particles, or between the particles and the hydrophilic fibers within the absorbent structure. This phenomenon is often referred to as a form of gel-blocking and may occur as a result of the superabsorbent material lacking sufficient gel integrity or reaching such a high degree of swelling that it tends to be easily deformable under an external pressure, such as those loads applied by a wearer during movement or upon sitting down.

The in-use performance of an absorbent structure may therefore rely upon 1) the ability to create open channels and void volume within the absorbent structure and 2) the ability to maintain the openness of and accessibility to such channels and void volume upon saturation of the absorbent structure. The ability to create the open channels may be a function of the ability of the superabsorbent material to absorb liquid while the material is under pressure as well as the ability to retain liquid and not deform while under pressure. Liquid handling characteristics commonly associated with such functions include the retention capacity (CRC) and the absorbency under load (AUL) value of the superabsorbent material. The ability to maintain openness of and accessibility to the channels and void volume may be in large part a function of the gel bed permeability (GBP) of the superabsorbent material. A higher GBP indicates a higher ability to maintain open channels within the absorbent structure after the superabsorbent material is saturated and fully swollen.

To date, research efforts directed toward improving the liquid handling characteristics of absorbent structures have generally been focused on enhancing the gel bed permeability of the superabsorbent material within absorbent structures. However, such an approach has come at a cost in the form of reduced or at least a lack of enhanced retention capacity.

There is a need, therefore, for absorbent structures incorporating superabsorbent materials having a high gel bed permeability, a high retention capacity and/or a high absorbency under load value.

SUMMARY OF THE INVENTION

In one embodiment, an absorbent structure of the present invention generally comprises at least in part a superabsorbent material having a retention capacity (CRC) as determined by a Centrifuge Retention Capacity Test of at least about 25 g/g and a free swell gel bed permeability (GBP) as determined by a Free Swell Gel Bed Permeability Test of at least $575 \times 10^{-9}$ cm$^2$.

In another embodiment, an absorbent structure of the present invention generally comprises at least in part a superabsorbent material having a retention capacity (CRC) as determined by a Centrifuge Retention Capacity Test of at least about 25 g/g, an absorbency under load (AUL) at 0.9 psi as determined by an Absorbency Under Load Test of at least 18 and a free swell gel bed permeability (GBP) as determined by a Free Swell Gel Bed Permeability Test of at least about $350 \times 10^{-9}$ cm$^2$.

Other features of the invention will be in part apparent and in part pointed out hereinafter.

DEFINITIONS

Within the context of this specification, each term or phrase below will include the following meaning or meanings:

"Bi-component," or "Multi-component" fibers as used herein refers to fibers formed from two (e.g., bi-component) or more components, such as a natural fiber and a polymer or two or more polymers extruded from one or more separate extruders, joined together to form a single fiber. The components are arranged in substantially constantly positioned distinct zones across a cross-section of the multi-component fibers and extend continuously along at least a portion of, and more desirably the entire, length of the fiber. The configuration of the multi-component fibers may be, for example, a sheath/core arrangement in which one polymer is surrounded by another, a side-by-side arrangement, a pie arrangement, an "islands-in-the-sea" arrangement or other suitable arrangement. Bi-component fibers are disclosed in U.S. Pat. No. 5,108,820 to Kaneko et al., U.S. Pat. No. 4,795,668 to Krueger et al., U.S. Pat. No. 5,540,992 to Marcher et al. and U.S. Pat. No. 5,336,552 to Strack et al. Bi-component fibers are also taught in U.S. Pat. No. 5,382,400 to Pike et al. and may be used to produce crimp in the fibers by using the differential rates of expansion and contraction of the two (or more) polymers.

"Bonded-Carded" refers to webs that are made from staple length fibers which are sent through a combing or carding unit, which separates or breaks apart and aligns the fibers in the machine direction to form a generally machine direction-oriented fibrous non-woven web. This material may be bonded together by methods that include point bonding, through air bonding, ultrasonic bonding, adhesive bonding or other suitable bonding technique.

"Hydrophilic" describes a material or surface which is wetted by aqueous liquids in contact therewith. The degree of wetting can, in turn, be described in terms of the contact angles and the surface tensions of the liquids and materials involved. Equipment and techniques suitable for measuring the wettability of particular materials or surfaces can be provided by a Cahn SFA-222 Surface Force Analyzer System, or a substantially equivalent system. When measured with this system, materials or surfaces having contact angles less than 90 degrees are designated "wettable" or hydrophilic, and those having contact angles greater than 90 degrees are designated "nonwettable" or hydrophobic.

"Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al, which is incorporated herein by reference. Meltblown fibers are typically microfibers which may be continuous or discontinuous, are generally about 0.6 denier or smaller, and are generally self-bonding when deposited onto a collecting surface.

"Non-woven" or "non-woven web" refers to materials or webs that are formed without the aid of a textile weaving or knitting process. The structure comprises individual or groups of fibers or threads which are interlaid, but not in an identifiable manner as in a knitted fabric. Non-woven structures have been formed from many processes such as, for example, meltblowing processes, spunbonding processes, and bonded-carded processes.

"Spunbond" refers to small diameter fibers which are formed by extruding molten thermoplastic material as filaments from a plurality of fine capillaries of a spinneret having a circular or other configuration, with the diameter of the extruded filaments then being rapidly reduced by an air-drawing process such as that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers of about 0.3 or larger, more particularly, between about 0.6 and about 10.

"Superabsorbent" and "Superabsorbent Material" refer to a water-swellable, water-insoluble organic or inorganic polymer and/or material capable, under the most favorable conditions, of absorbing at least about 10 times its weight and, more suitably, at least about 30 times its weight in an aqueous solution containing 0.9 weight percent sodium chloride solution in water. A superabsorbent polymer is a crosslinked polymer which is capable of absorbing large amounts of aqueous liquids and body fluids, such as urine or blood, with swelling and the formation of hydrogels, and of retaining such liquids and fluids under pressure in accordance with the present definition of the term superabsorbent.

"Thermoplastic" describes a material that softens when exposed to heat and which substantially returns to a nonsoftened condition when cooled to room temperature.

DETAILED DESCRIPTION

Figure 1:
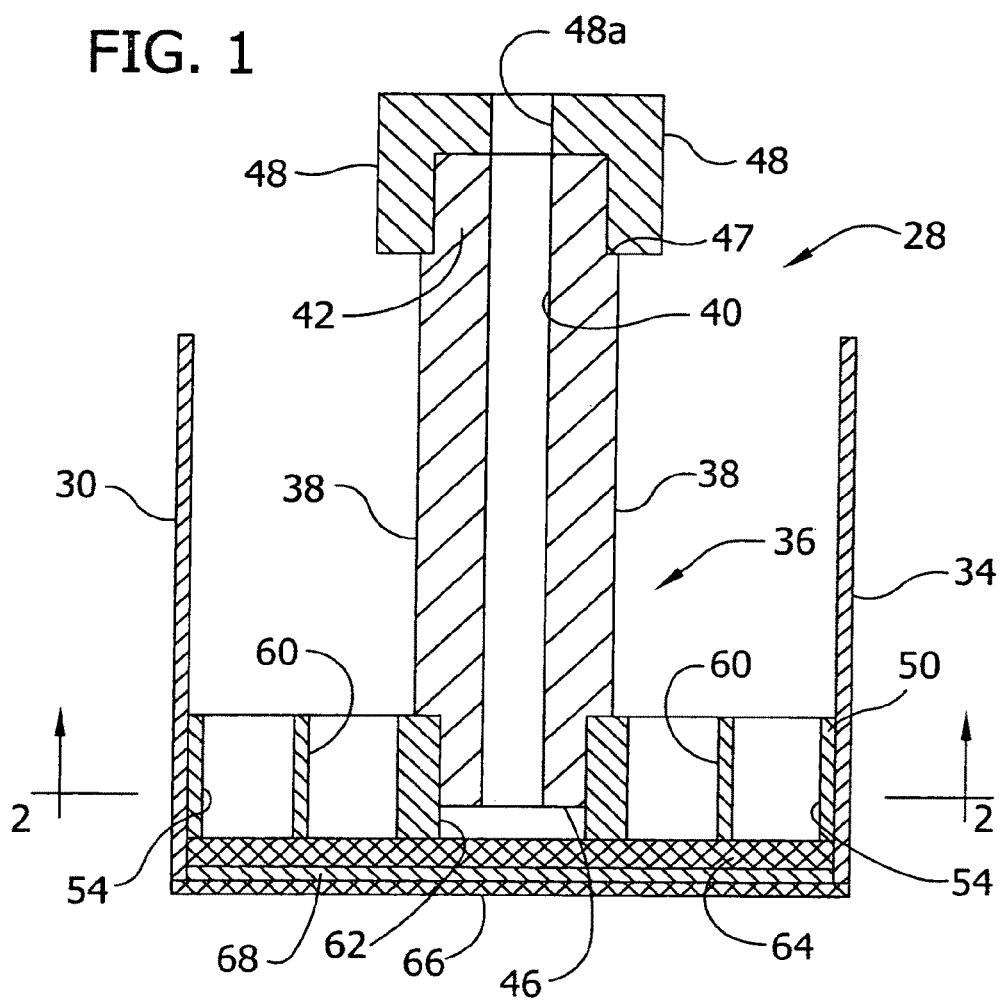
FIG. 1 is a cross-section of apparatus for conducting a Permeability Test.

The present invention is directed generally to absorbent structures having enhanced liquid handling properties, and more particularly to absorbent structures containing a superabsorbent material that has both a high liquid retention capacity and a high free swell gel bed permeability. The present invention is also directed generally to absorbent articles incorporating these absorbent structures. For example, such absorbent articles include, without limitation, feminine care pads, interlabial products, tampons, diapers, incontinence articles such as pads, guards, pants and undergarments, training pants, medical garments, bed pads, sweat absorbing pads, shoe pads, bandages, helmet liners, wipes, etc. As another example, the absorbent structure may be useful by itself, such as in the form of a tissue, towel, napkin or the like.

In one embodiment, the absorbent structure is a non-woven web comprising hydrophilic fibers and superabsorbent material. Examples of suitable hydrophilic fibers include naturally occurring organic fibers composed of intrinsically wettable material, such as cellulosic fibers. Suitable sources of cellulosic fibers include: wood fibers, such as bleached kraft softwood or hardwood, high-yield wood fibers, and ChemiThermoMechanical Pulp fibers; bagasse fibers; milkweed fluff fibers; wheat straw; kenaf; hemp; pineapple leaf fibers; or peat moss. Other hydrophilic fibers, such as regenerated cellulose and curled chemically stiffened cellulose fibers may also be densified to form absorbent structures that can expand to a higher loft when wetted. Pulp fibers may also be stiffened by the use of crosslinking agents such as formaldehyde or its derivatives, glutaraldehyde, epichlorohydrin, methylolated compounds such as urea or urea derivatives, anhydrides such as maleic anhydride, non-methylolated urea derivatives, citric acid or other polycarboxylic acids.

One example of a suitable hydrophilic fiber is available from Bowater of Coosa River, Ala., U.S.A. as model designation CR1654 and is a bleached, highly absorbent sulfate wood pulp containing primarily soft wood fibers. Another suitable hydrophilic fiber is available from Weyerhauser of Federal Way, Wash., U.S.A. as model designation NB-416 and is a bleached southern softwood pulp.

Other examples of suitable hydrophilic fibers include synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material that has a suitable hydrophilic moiety and is not readily removable from the fiber, or by sheathing a nonwettable, hydrophobic fiber with a hydrophilic polymer during or after the formation of the fiber.

For the purposes of the present invention, it is contemplated that selected blends of the various types of fibers mentioned above may also be employed. Moreover, the fiber selection may instead, or may additionally, include bi-component or bi-constituent fibers that are hydrophilic or have been treated to be hydrophilic and are used to enhance the integrity and/or softness of the absorbent structure by bonding through heat activation.

It is also contemplated that the absorbent structure may instead, or may additionally, comprise hydrophobic fibers without departing from the scope of this invention. In another embodiment, the absorbent structure may comprise only a superabsorbent material, such as by being formed the structure using conventional foaming techniques.

Suitable superabsorbent materials may be selected from natural, biodegradable, synthetic and modified natural polymers and materials. In addition, the superabsorbent material may comprise inorganic materials, such as silica gels, or organic compounds such as crosslinked polymers. The term "crosslinked" used in reference to the superabsorbent material refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

In one embodiment, the superabsorbent material comprises a crosslinked superabsorbent polymer or combination of polymers comprising a) from about 55 to about 99.9 weight (wt.) percent of polymerizable unsaturated acid group containing monomers; b) from about 0.001 to about 5.0 wt. percent of internal crosslinking agent; c) from about 0.001 to about 5.0 wt. percent of a surface crosslinking agent applied to the particle surface; d) from 0 to about 5 wt. percent of a penetration modifier applied to the surface of the particle immediately before, during or immediately after surface crosslinking; e) from 0 to about 5 wt. percent of a multivalent metal salt on the surface; f) from about 0.01 to about 5 wt. percent of an insoluble, inorganic powder; and g) from about 0 to about 2 wt. percent surface active agent on the surface, wherein the superabsorbent material has a degree of neutralization of more than about 25 percent.

The crosslinked superabsorbent polymer is obtained by the initial polymerization of from about 55 to about 99.9 wt. percent of polymerizable unsaturated acid group containing monomers. Suitable monomers include those containing carboxyl groups, such as acrylic acid, methacrylic acid or 2-acrylamido-2-methylpropanesulfonic acid, or mixtures of these monomers are preferred here. It is preferable for at least about 50 wt. %, and more preferably at least about 75 wt. % of the acid groups to be carboxyl groups. The acid groups are neutralized to the extend of at least about 25 mol %, that is, the acid groups are preferably present as sodium, potassium or ammonium salts. The degree of neutralization is preferably at least about 50 mol %. It is preferred to obtain polymers obtained by polymerization of acrylic acid or methacrylic acid, the carboxyl groups of which are neutralized to the extent of 50-80 mol %, in the presence of internal crosslinking agents.

Further monomers, which can be used for the preparation of the superabsorbent polymers, are 0-40 wt. % of ethylenically unsaturated monomers which can be copolymerized with a) as set forth above, such as e.g. acrylamide, methacrylamide, hydroxyethyl acrylate, dimethylaminoalkyl (meth)-acrylate, ethoxylated (meth)-acrylates, dimethylaminopropylacrylamide or acrylamidopropyltrimethylammonium chloride. More than 40 wt. % of these monomers can impair the swellability of the polymers.

The internal crosslinking agent has at least two ethylenically unsaturated double bonds or one ethylenically unsaturated double bond and one functional group which is reactive towards acid groups of the polymerizable unsaturated acid group containing monomers or several functional groups which are reactive towards acid groups can be used as the internal crosslinking component and which is present during the polymerization of the polymerizable unsaturated acid group containing monomers.

Examples of internal crosslinking agents include aliphatic unsaturated amides, such as methylenebisacryl- or -methacrylamide or ethylenebisacrylamide, and furthermore aliphatic esters of polyols or alkoxylated polyols with ethylenically unsaturated acids, such as di(meth)acrylates or tri(meth)acrylates or butanediol or ethylene glycol, polyglycols or trimethylolpropane, di- and triacrylate esters of trimethylolpropane which is preferably oxyalkylated, preferably ethoxylated, with 1 to 30 mol of alkylene oxide, acrylate and methacrylate esters of glycerol and pentaerythritol and of glycerol and pentaerythritol oxyethylated with preferably 1 to 30 mol of ethylene oxide and furthermore alkyl compounds, such as alkyl(meth)acrylate, alkoxylated allyl(meth)acrylate reacted with preferably 1 to 30 mol of ethylene oxide, trially cyanurate, triallyl isocyanurate, maleic acid diallyl ester, poly-allyl esters, tetraallyloxyethane, traillylamine, tetraallylethylenediamine, diols, polyols, hydroxyl allyl or acrylate compounds and allyl esters of phosphoric acid or phosphorous acid, and furthermore monomers which are capable of crosslinking, such as N-methylol compounds of unsaturated amides, such as of methacrylamide or acrylamide, and the esthers derived there from. Ionic crosslinkers such as multivalent metal salts may also be employed. Mixtures of the crosslinking agents mentioned can also be employed. The content of the internal crosslinking agents is from about 0.01 to about 5 wt. %, and preferably from about 0.1 to about 3.0 wt. %, based on the total amount of the polymerizable unsaturated acid group containing monomers.

Initiators, such as e.g. azo or peroxo compounds, redox systems or UV initiators, (sensitizers), and/or radiation are used for initiation of the free-radical polymerization.

The superabsorbent polymer is surface crosslinked after polymerization. Surface crosslinking refers to any process that increases the crosslinking density of the polymer matrix in the vicinity of the superabsorbent particle surface with respect to the crosslinking density of the particle interior. The superabsorbent polymers are typically surface crosslinked by the addition of a surface crosslinking agent. Preferred surface crosslinking agents include chemicals with one or more functional groups, which are reactive towards pendant groups of the polymer chains, typically the acid groups. The content of the surface crosslinking agents is from about 0.01 to about 5 wt. %, and more suitably from about 0.1 to about 3.0 wt. %, based on the weight of the dry polymer. A heating step is preferred after addition of the surface crosslinking agent.

The superabsorbent polymer can be coated with an alkaline carbonate followed by heating to effect surface crosslinking to improve the surface crosslinking density and the gel strength characteristics of the superabsorbent material. More specifically a surface crosslinking agent is coated onto the superabsorbent particle by mixing the polymer with an aqueous alcoholic solution of the alkylene carbonate surface crosslinking agent. The amount of alcohol is determined by the solubility of the alkylene carbonate and is kept as low as possible for technical reasons, for instance protection against explosions. Suitable alcohols are methanol, ethanol, butanol, or butyl glycol as well as mixtures of these alcohols. The preferred solvent is water, which typically is used in an amount of 0.3 to 5.0% by weight, relative to particulate superabsorbent polymer. In some instances, the alkylene carbonate surface crosslinking agent is dissolved in water, without any alcohol. It is also possible to apply the alkylene carbonate surface crosslinking agent from a powder mixture, for example, with an inorganic carrier material, such as $SiO_2$, or in the vapor state by sublimation of the alkylene carbonate.

To achieve the desired surface crosslinking properties, the alkylene carbonate is suitably distributed evenly on the particulate superabsorbent polymer. For this purpose, mixing is effected in suitable mixers, such as fluidized bed mixers, paddle mixers, milling rolls, or twin-worm mixers. It is also possible to carry out the coating of the particulate superabsorbent polymer during one of the process steps in the production of the particulate superabsorbent polymer. A particularly suitable process for this purpose is the inverse suspension polymerization process.

The thermal treatment, which follows the coating treatment, is carried out as follows. In general, the thermal treatment is at a temperature between 100 and 300° C. However, if the alkylene carbonates are used, then the thermal treatment is suitably at a temperature between 150 and 250° C. The treatment temperature depends on the dwell time and the kind of alkylene carbonate. At a temperature of 150° C., the thermal treatment is carried out for one hour or longer. On the other hand, at a temperature of 250° C., a few minutes, e.g., 0.5 to 5 minutes, are sufficient to achieve the desired surface crosslinking properties. The thermal treatment may be carried out in conventional dryers or ovens.

While particles are used by way of example as the physical form of the superabsorbent polymer, the invention is not limited to this form and is applicable to other forms such as fibers, foams, films, beads, rods and the like.

The superabsorbent polymer can comprise from 0 to about 5 wt. % of a penetration modifier that is added immediately before, during or immediately after the surface crosslinking agent. Examples of penetration modifiers include compounds which alter the penetration depth of surface-modifying agents in to the superabsorbent polymer particle, fiber, film, foam or bead by changing the viscosity, surface tension, ionic character or adhesion of said agents or medium in which these agents are implied. Preferred penetration modifiers are polyethylene glycols, tetraethylene glycol dimethyl ether, monovalent metal salts, surfactants and water soluble polymers.

The superabsorbent polymer according to the invention can comprise from 0 to about 5 wt. % of a multivalent metal salt, based on the weight of the mixture, on the surface of the polymer. The multivalent metal salt is preferably water soluble. Examples of preferred metal cations include cations of Al, Fe, Zr, Mg and Zn. Preferably, the metal cation has a valence of at least +3, with Al being most suitable. Examples of suitable anions in the multivalent metal salt include halides, chlorohydrates, sulfates, nitrates and acetates, with chlorides, sulfates, chlorohydrates and acetates being preferred, chlorohydrates and sulfates being more preferred and sulfates being the most preferred. Aluminum sulfate is the most suitable multivalent metal salt and is readily commercially available. A suitable form of aluminum sulfate is hydrate aluminum sulfate, preferably aluminum sulfate having from 12 to 14 waters of hydration. It is understood that mixtures of multivalent metal salts can be employed and remain within the scope of this invention.

The polymer and multivalent metal salt are suitably mixed by dry blending, or more suitably by being blended in solution, and most suitably an aqueous solution, using means well known to those skilled in the art. With dry blending, a binder may be employed in an amount sufficient to ensure that a substantially uniform mixture of the salt and the polymer is maintained. The binder may be water or a nonvolatile organic compound having a boiling point of at least 150° C. Examples of suitable binders include water, polyols such a propylene glycol, glycerin and polyethylene glycol).

The superabsorbent polymer can also comprise from about 0.01 to about 5 wt. % of water-insoluble, inorganic powder. Examples of suitable water-insoluble, inorganic powders include silicon dioxide, silicic acid, silicates, titanium dioxide, aluminum oxide, magnesium oxide, zinc oxide, talc, calcium phosphate, clays, diatomataceous earth, zeolites, bentonite, kaolin, hydratalcite, activated clays, etc. The insoluble inorganic powder additive may be a single compound or a mixture of compounds selected from the above list. Of all of these examples, microscopic noncrystal silicon dioxide or aluminum oxide are most suitable. Further, a suitable particle diameter of the inorganic powder is 1,000 μm or smaller, and more suitably 100 μm or smaller.

The superabsorbent polymer may also include the addition of from 0 to about 5 wt. % of a surfactant to the polymer particle surface. It is preferred that these be added immediately prior to, during or immediately after the surface crosslinking step. Examples of such surfactants include anionic, non-ionic, cationic and amphoteric surface active agents, such as fatty acid salts, dialykl sulfo-succinate, alkyl phosphate salt, and polyoxyethylene alkyl sulfate sale; polyoxyethylene alkyl ether, polyoxyethylene alkyl phenol ether, polyoxyethylene fatty acid ester, sorbitan fatty acid ester, polyoxy sorbitan fatty acid ester, polyoxyethylene alkylamine, fatty acid esters, and oxyethylene-oxypropylene block polymer; alkyl amine salts, quaternary ammonium salts; and lauryl dimethylamine oxide. However, it is not necessary to restrict the surfactant to those mentioned above. Such surfactants may be used individually, or in combination.

The superabsorbent polymer may also include from 0 to about 30 wt. % of water-soluble polymer, such as partly or completely hydrolyzed polyvinyle acetate, polyvinylpyrrolidone, starch or starch derivatives, polyglycols or polyacrylic acids, preferably in polymerized-in form. The molecular weight of these polymers is not critical as long as they are water-soluble. Preferred water-soluble polymers are starch and polyvinyl alcohol. The preferred content of such water-soluble polymers in the absorbent polymer according to the invention is 0-30 wt. %, preferably 0-5 wt. %, based on the total amount of components a) to d). The water-soluble polymers, preferably synthetic polymers, such as polyvinyl alcohol, can also serve as a graft base for the monomers to be polymerized.

It is sometimes desirable to employ surface additives that perform several roles during surface modifications. For example, a single additive may be a surfactant, viscosity modifier and react to crosslink polymer chains.

The superabsorbent polymer may also include from 0 to about 2.0 wt. % of dedusting agents, such as hydrophilic and hydrophobic dedusting agents such as those described in U.S. Pat. Nos. 6,090,875 and 5,994,440.

Further additives may optionally be employed, e.g., odor-binding substances such as cyclodextrins, zeolites, inorganic or organic salts and similar materials; anti-caking additives, flow modification agents and the like.

The superabsorbent polymer is suitably prepared by two methods. The polymer can be prepared continuously or discontinuously in a large-scale industrial manner by the above-mentioned known process, the after-crosslinking being carried out accordingly.

According to the first method, the partly neutralized monomer, suitably acrylic acid, is converted into a gel by free-radical polymerization in aqueous solution in the presence of crosslinking agents and optionally further components, and the gel is comminuted, dried, ground and sieved off to the desired particle size. This solution polymerization can be carried out continuously or discontinuously.

Inverse suspension and emulsion polymerization can also be used for preparation of the superabsorbent polymer. According to these processes, an aqueous, partly neutralized solution of monomers, preferably acrylic acid, is dispersed in a hydrophobic, organic solvent with the aid of protective colloids and/or emulsifiers and the polymerization is started by free radical initiators. The internal crosslinking agents are either dissolved in the monomer solution and metered in together with this, or are added separately and optionally during the polymerization. The addition of a water-soluble polymer as the graft base optionally takes place via the monomer solution or by direct introduction into the oily phase. The water is then removed azeotropically from the mixture and the polymer is filtered off and optionally dried. Internal crosslinking can be carried out by polymerizing in a polyfunctional crosslinking agent dissolved in the monomer solution and/or by reaction of suitable crosslinking agents with functional groups of the polymer during the polymerization steps.

In one particular embodiment, the superabsorbent material suitable for use in the absorbent structure of the present invention comprises a crosslinked superabsorbent polymer comprising either at least about 75 weight percent anionic polymer/polymers or at least about 75 weight percent cationic polymer/polymers. More suitably, the superabsorbent material comprises a crosslinked polymer comprising either at least about 85 weight percent anionic polymer/polymers or at least about 85 weight percent cationic polymer/polymers, and even more suitably either at least about 90 weight percent anionic polymer/polymers or at least about 90 weight percent cationic polymer/polymers.

An anionic polymer is intended to refer to a polymer comprising a functional group or groups capable of becoming negatively charged ions upon ionization in an aqueous solution. In general, suitable functional groups for an anionic polymer include, but are not limited to, carboxyl groups, sulfonate groups, sulphate groups, sulfite groups, and phosphate groups. Suitably, the functional groups are carboxyl groups. It is preferred that these functional groups are in neutralized form. A suitable degree of neutralization is at least 50%, more suitably at least 60%, and even more suitably at least 70%.

A cationic polymer is intended to refer to a polymer comprising a functional group or groups capable of becoming positively charged ions upon ionization in an aqueous solution. In general, suitable functional groups for a cationic polymer include, but are not limited to, primary, secondary, or tertiary amino groups, imino groups, imido groups, amido groups, and quaternary ammonium groups. It is suitable that these functional groups are in neutralized form. A suitable degree of neutralization is at least 50%, more suitably at least 60%, and even more suitably at least 70%.

Examples of synthetic anionic superabsorbent polymers include the alkali metal and ammonium salts or partial salts of poly(acrylic acid), poly(methacrylic acid), hydrolyzed poly(acrylamides), maleic anhydride copolymers with vinyl ethers and alpha-olefins, poly(vinyl acetic acid), poly(vinyl sulfonic acid), poly(vinyl phosphonic acid), poly(vinyl ethers), poly(vinyl pyrrolidone), poly(vinylmorpholinone), poly(vinyl alcohol), and mixtures and copolymers thereof. Examples of natural based anionic polymers include the salts or partial salts of carboxymethyl cellulose, carboxymethyl starch, alginates, and carrageenans. Also, synthetic polypeptides such as polyaspartic acid and polyglutamic acid can be examples of the anionic polymers. Examples of synthetic cationic superabsorbent polymers include the salts or partial salts of poly(vinyl amines), poly(allylamines), polyethylene imine), poly(amino proanol vinyl ethers), poly(acrylamidopropyl trimethyl ammonium chloride), poly(diallyldimethyl ammonium chloride). Examples of natural based cationic polymers include partially deacetalated chitin, chitosan and chitosan salts. Also synthetic polypeptides such as polyasparagins, polylysines, polyglutamines, polyarginines can be examples of the cationic polymers.

In one embodiment, the superabsorbent material used in making the absorbent structure is in the form of discrete particles. Superabsorbent material particles can be of any suitable shape, for example, spiral or semi-spiral, cubic, rod-like, polyhedral, etc. Particle shapes having a large greatest dimension/smallest dimension ratio, like needles, flakes, and fibers, are also contemplated for use herein. Conglomerates of particles of superabsorbent material may also be used in the absorbent structure. The superabsorbent materials may be of various length and cross-sectional dimensions.

In accordance with the present invention, the superabsorbent materials have certain liquid handling characteristics, including a suitable free swell gel bed permeability (GBP), a suitable absorbency under load value (AUL), a suitable centrifuge retention capacity (CRC), a suitable absorption against pressure (AAP) value and a suitable shear modulus (G'), all of which are measurable using the following tests.

Free Swell Gel Bed Permeability Test

Figure 2:
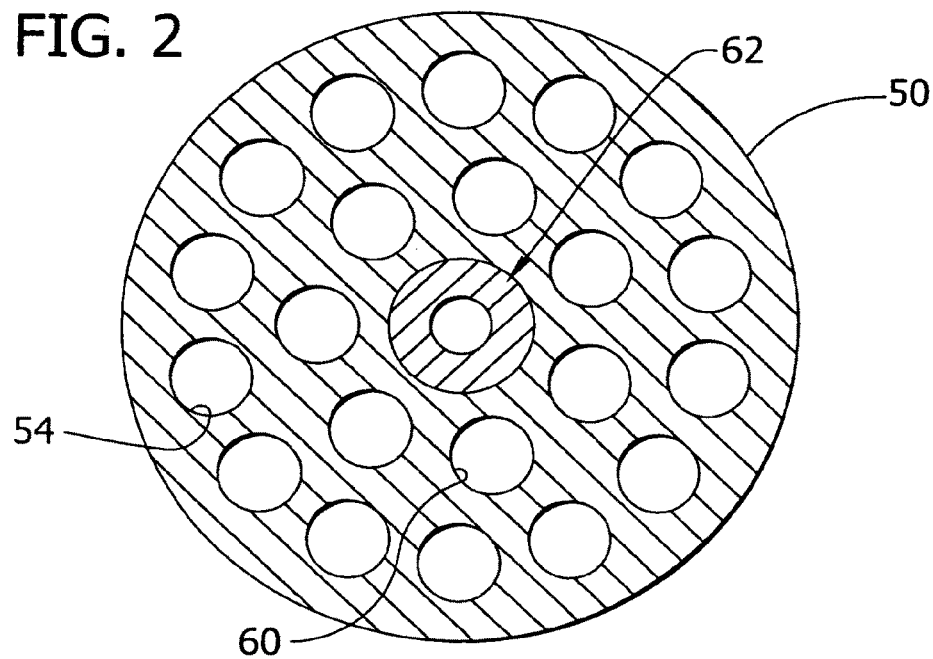
FIG. 2 is a section taken in the plane of line 2-2 of FIG. 1.

As used herein, the Free Swell Gel Bed Permeability (GBP) Test determines the permeability of a swollen bed of superabsorbent material under what is commonly referred to as "free swell" conditions. The term "free swell" means that the superabsorbent material is allowed to swell without a swell restraining load upon absorbing test solution as will be described. A suitable apparatus for conducting the Free Swell Gel Bed Permeability Test is shown in FIGS. 1 and 2 and indicated generally at 28. The test apparatus 28 comprises a sample container, generally indicated at 30, and a piston, generally indicated at 36. The piston 36 comprises a cylindrical LEXAN shaft 38 having a concentric cylindrical hole 40 bored down the longitudinal axis of the shaft. Both ends of the shaft are machined to provide upper and lower ends respectively designated 42, 46. A weight, indicated as 48, rests on one end 42 and has a cylindrical hole 48a bored through at least a portion of its center.

A circular piston head 50 is positioned on the other end 46 and is provided with a concentric inner ring of seven holes 60, each having a diameter of about 0.95 cm, and a concentric outer ring of fourteen holes 54, also each having a diameter of about 0.95 cm. The holes 54, 60 are bored from the top to the bottom of the piston head 50. The piston head 50 also has a cylindrical hole 62 bored in the center thereof to receive end 46 of the shaft 38. The bottom of the piston head 50 may also be covered with a biaxially stretched 400 mesh stainless steel screen 64.

The sample container 30 comprises a cylinder 34 and a 100 mesh stainless steel cloth screen 66 that is biaxially stretched to tautness and attached to the lower end of the cylinder. A superabsorbent material sample, indicated as 68 in FIG. 1, is supported on the screen 66 within the cylinder 34 during testing.

The cylinder 34 may be bored from a transparent LEXAN rod or equivalent material, or it may be cut from a LEXAN tubing or equivalent material, and has an inner diameter of about 6 cm (e.g., a cross-sectional area of about 28.27 cm$^2$), a wall thickness of about 0.5 cm and a height of approximately 5 cm. Drainage holes (not shown) are formed in the sidewall of the cylinder 34 at a height of approximately 4.0 cm above the screen 66 to allow liquid to drain from the cylinder to thereby maintain a fluid level in the sample container at approximately 4.0 cm above the screen 66. The piston head 50 is machined from a LEXAN rod or equivalent material and has a height of approximately 16 mm and a diameter sized such that it fits within the cylinder 34 with minimum wall clearance but still slides freely. The shaft 38 is machined from a LEXAN rod or equivalent material and has an outer diameter of about 2.22 cm and an inner diameter of about 0.64 cm.

The shaft upper end 42 is approximately 2.54 cm long and approximately 1.58 cm in diameter, forming an annular shoulder 47 to support the weight 48. The annular weight 48 has an inner diameter of about 1.59 cm so that it slips onto the upper end 42 of the shaft 38 and rests on the annular shoulder 47 formed thereon. The annular weight 48 can be made from stainless steel or from other suitable materials resistant to corrosion in the presence of the test solution, which is 0.9 wt. % sodium chloride solution in distilled water. The combined weight of the piston 36 and annular weight 48 equals approximately 596 grams (g), which corresponds to a pressure applied to the sample 68 of about 0.3 pounds per square inch (psi), or about 20.7 dynes/cm$^2$, over a sample area of about 28.27 cm$^2$.

When the test solution flows through the test apparatus during testing as described below, the sample container 30 generally rests on a 16 mesh rigid stainless steel support screen (not shown). Alternatively, the sample container 30 may rest on a support ring (not shown) diametrically sized substantially the same as the cylinder 34 so that the support ring does not restrict flow from the bottom of the container.

To conduct the Gel Bed Permeability Test under "free swell" conditions, the piston 36, with the weight 48 seated thereon, is placed in an empty sample container 30 and the height from the bottom of the weight 48 to the top of the cylinder 34 is measured using a caliper or suitable gauge accurate to 0.01 mm. It is important to measure the height of each sample container 30 empty and to keep track of which piston 36 and weight 48 is used when using multiple test apparatus. The same piston 36 and weight 48 should be used for measurement when the sample 68 is later swollen following saturation.

The sample to be tested is prepared from superabsorbent material particles which are prescreened through a U.S. standard 30 mesh screen and retained on a U.S. standard 50 mesh screen. As a result, the test sample comprises particles sized in the range of about 300 to about 600 microns. The particles can be prescreened by hand or automatically. Approximately 0.9 grams of the sample is placed in the sample container 30, and the container, without the piston 36 and weight 48 therein, is then submerged in the test solution for a time period of about 60 minutes to saturate the sample and allow the sample to swell free of any restraining load.

At the end of this period, the piston 36 and weight 48 assembly is placed on the saturated sample 68 in the sample container 30 and then the sample container 30, piston 36, weight 48, and sample 68 are removed from the solution. The thickness of the saturated sample 68 is determined by again measuring the height from the bottom of the weight 48 to the top of the cylinder 34, using the same caliper or gauge used previously provided that the zero point is unchanged from the initial height measurement. The height measurement obtained from measuring the empty sample container 30, piston 36, and weight 48 is subtracted from the height measurement obtained after saturating the sample 68. The resulting value is the thickness, or height "H" of the swollen sample.

The permeability measurement is initiated by delivering a flow of the test solution into the sample container 30 with the saturated sample 68, piston 36, and weight 48 inside. The flow rate of test solution into the container is adjusted to maintain a fluid height of about 4.0 cm above the bottom of the sample container. The quantity of solution passing through the sample 68 versus time is measured gravimetrically. Data points are collected every second for at least twenty seconds once the fluid level has been stabilized to and maintained at about 4.0 cm in height. The flow rate Q through the swollen sample 68 is determined in units of grams/second (g/s) by a linear least-square fit of fluid passing through the sample 68 (in grams) versus time (in seconds).

Permeability in cm$^2$ is obtained by the following equation:

$$K=[Q*H*Mu]/[A*Rho*P]$$

where K=Permeability (cm$^2$), Q=flow rate (g/sec), H=height of sample (cm), Mu=liquid viscosity (poise) (approximately one centipoises for the test solution used with this Test), A=cross-sectional area for liquid flow (cm$^2$), Rho=liquid density (g/cm$^3$) (approximately one g/cm$^3$, for the test solution used with this Test) and P=hydrostatic pressure (dynes/cm$^2$) (normally approximately 3,923 dynes/cm$^2$). The hydrostatic pressure is calculated from $$P=Rho*g*h$$

where Rho=liquid density (g/cm$^3$), g=gravitational acceleration, nominally 981 cm/sec$^2$, and h=fluid height, e.g., 4.0 cm for the Free Swell Gel Bed Permeability Test described herein.

A minimum of three samples is tested and the results are averaged to determine the free swell gel bed permeability of the sample. The samples are tested at 23±1 degrees Celcius at 50±2 percent relative humidity.

Absorbency Under Load Test

Figure 3:
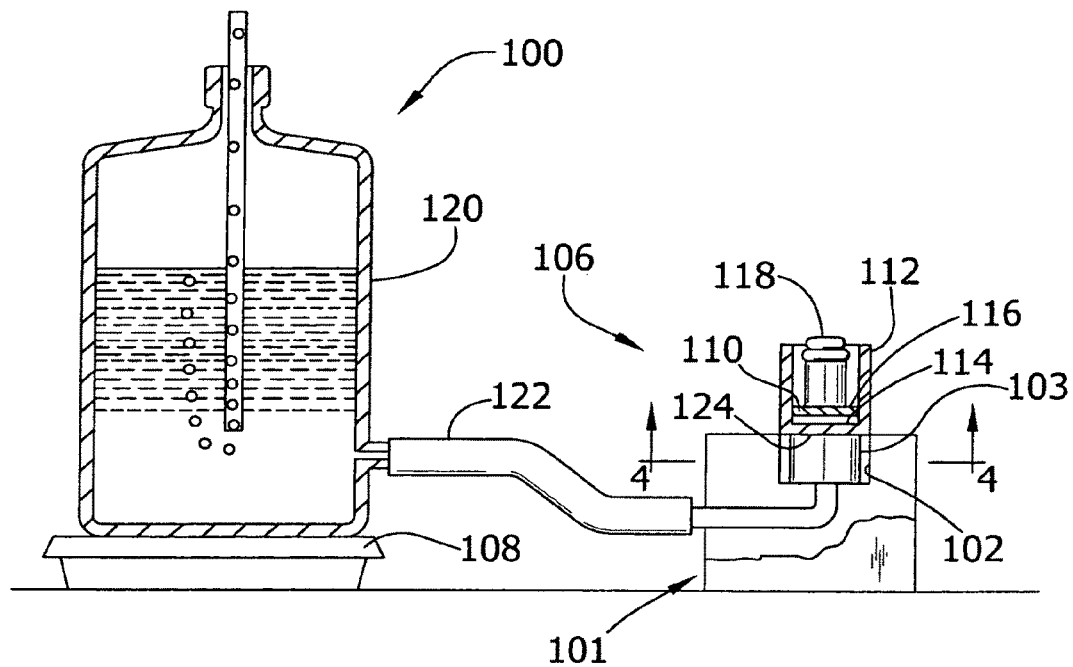
FIG. 3 is a cross-section of apparatus for conducting an Absorbency Under Load Test.

The Absorbency Under Load (AUL) Test measures the ability of the superabsorbent material to absorb a 0.9 weight percent solution of sodium chloride in distilled water at room temperature (test solution) while the material is under a 0.9 psi load. Apparatus 106 for conducting the AUL Test is shown in FIG. 3 and comprises a Demand Absorbency Tester (DAT), generally indicated at 100, which is similar to the Gravimetric Absorbency Test System (GATS) available from M/K Systems of Danners, Mass., U.S.A., and to the system described by Lichstein at pages 129-142 of the INDA Technological Symposium Proceedings, March 1974.

Figure 4:
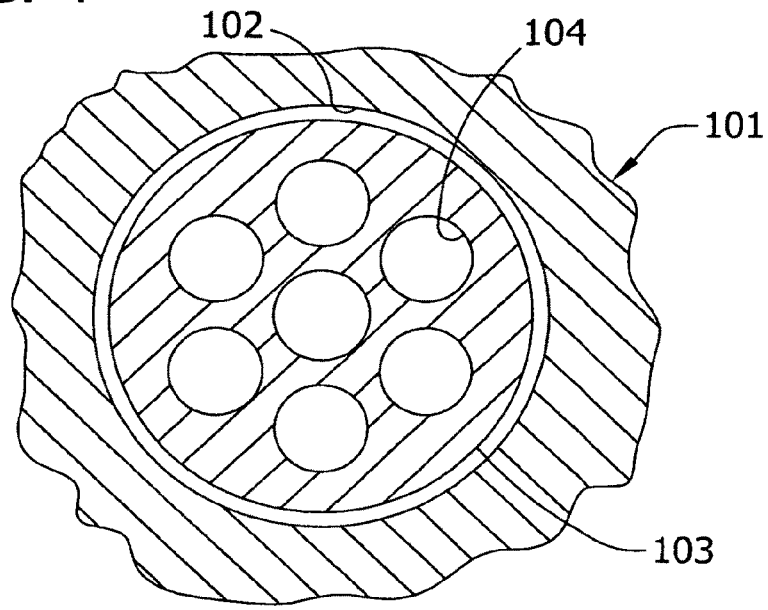
FIG. 4 is a section taken in the plane of line 4-4 of FIG. 3.

The test apparatus further comprises a test stand, generally indicated at 101 (FIG. 4) having a cavity 102 formed therein and a porous plate 103 seated in the cavity and having a central porous area of about 2.54 cm diameter formed by a plurality of bores 104 extending through the plate. The cavity 102 shown in FIG. 4 has a diameter of about 3.2 cm and the porous plate 103 has a diameter of about 3.1 cm and comprises seven bores 104, each having a diameter of about 0.3 cm. One of the bores 104 is centrally located and the remaining six bores are concentrically positioned about the central bore with the spacing from the center of the central bore to the center of each adjacent bore is about one centimeter.

A sample container for containing a sample 110 of superabsorbent material to be tested comprises a cylinder 112 and a stainless steel cloth screen 114 that is biaxially stretched to tautness and attached to the lower end of the cylinder. The cylinder 112 may be bored from a transparent LEXAN rod or equivalent material, or it may be cut from a LEXAN tubing or equivalent material, and has an inner diameter of about one inch (about 2.54 cm). The stainless steel cloth screen 114 is suitably a 100 mesh screen.

A disc, or piston 116 is machined from a LEXAN rod, Plexiglas or equivalent material and has a diameter sized such that it fits within the cylinder 112 with minimum wall clearance but still slides freely. The height of the piston 116 is approximately 0.8 cm and the weight of the piston is suitably about 4.4 grams to provide a load over the cross-sectional area of the sample in the container of about 0.01 psi. A weight 118 is sized (e.g., having a diameter of about 2.5 cm) for seating on the piston 116 to increase the load (e.g., in addition to the weight of the piston) on the sample. For example, a weight of about 317 grams is used to provide a load (e.g., including the piston weight) of about 0.9 psi over the cross-sectional area of the sample in the container.

The cavity 102, and hence the porous plate 103, is in fluid communication with a reservoir 120 containing test solution (0.9 weight percent sodium chloride solution in distilled water at room temperature) via a suitable conduit 122. As shown in FIG. 3, the reservoir 120 is seated on an electrostatic balance 108.

A sample 110 of superabsorbent material weighing about 0.160 grams is prepared by screening the particles through a U.S. standard 30 mesh screen and retaining the particles on a U.S. standard 50 mesh screen so that the sample comprises particles in the size range of about 300 to about 600 microns. The sample is weighed on suitable weighing paper and then loaded into the sample container (with the piston 116 removed) so that the particles overlay the screen at the bottom of the container. The sample container is gently tapped to level the bed of particles in the container.

The AUL Test is initiated by placing a circular piece of GF/A glass filter paper 124 onto the porous plate 103 over the bores 104 formed therein and allowed to become saturated by test solution delivered from the reservoir 120 to the porous plate via the conduit 122. The paper 124 is suitably sized larger than the inner diameter of the cylinder 112 and smaller than the outer diameter thereof to ensure good contact while inhibiting evaporation over the bores 104. The electrostatic balance 108 is zeroed at this time. The piston 116 and weight 118 are placed on the sample within the container and the container (with the sample, piston and weight therein) is placed on the plate 103 over the saturated glass filter paper 124 to allow test solution to be taken into the sample in the container via the conduit 122, bores 104 in the plate 102 and the filter paper.

The electrostatic balance 108 is used to measure the flow of test solution to the sample over a period of about 60 minutes. The amount (in grams) of solution taken into the sample after about 60 minutes divided by the dry weight of the sample (e.g., about 0.160 grams) is the AUL value of the sample in grams of liquid per gram weight of sample.

Two checks can be made to ensure the accuracy of the measurement. First, the height the piston 116 rises above the screen 114 at the bottom of the sample container multiplied by the cross-sectional area of the piston should roughly equal the amount of solution picked up by the sample over the 60 minute period. Second, the sample container can be weighed before (e.g., while the superabsorbent material is dry) and after the test and the difference in weight should roughly equal the amount of solution picked up by the sample over the 60 minute period.

A minimum of three tests is performed and the results are averaged to determine the AUL value at 0.9 psi. The samples are tested at 23±1 degrees Celcius at 50±2 percent relative humidity.

Centrifuge Retention Capacity Test

The Centrifuge Retention Capacity (CRC) Test measures the ability of the superabsorbent material to retain liquid therein after being saturated and subjected to centrifugation under controlled conditions. The resultant retention capacity is stated as grams of liquid retained per gram weight of the sample (g/g). The sample to be tested is prepared from particles which are prescreened through a U.S. standard 30 mesh screen and retained on a U.S. standard 50 mesh screen. As a result, the sample comprises particles sized in the range of about 300 to about 600 microns. The particles can be prescreened by hand or automatically and are stored in a sealed airtight container until testing.

The retention capacity is measured by placing 0.2±0.005 grams of the prescreened sample into a water-permeable bag which will contain the sample while allowing a test solution (0.9 weight percent sodium chloride in distilled water) to be freely absorbed by the sample. A heat-sealable tea bag material, such as that available from Dexter Corporation of Windsor Locks, Conn., U.S.A., as model designation 1234T heat-sealable filter paper works well for most applications. The bag is formed by folding a 5-inch by 3-inch sample of the bag material in half and heat-sealing two of the open edges to form a 2.5-inch by 3-inch rectangular pouch. The heat seals should be about 0.25 inches inside the edge of the material. After the sample is placed in the pouch, the remaining open edge of the pouch is also heat-sealed. Empty bags are also made to serve as controls. Three samples (e.g., filled and sealed bags) are prepared for the test. The filled bags must be tested within three minutes of preparation unless immediately placed in a sealed container, in which case the filled bags must be tested within thirty minutes of preparation.

The bags are placed between two TEFLON® coated fiberglass screens having 3 inch openings (Taconic Plastics, Inc., Petersburg, N.Y.) and submerged in a pan of the test solution at 23 degrees Celsius, making sure that the screens are held down until the bags are completely wetted. After wetting, the samples remain in the solution for about 30±1 minutes, at which time they are removed from the solution and temporarily laid on a non-absorbent flat surface. For multiple tests, the pan should be emptied and refilled with fresh test solution after 24 bags have been saturated in the pan.

The wet bags are then placed into the basket of a suitable centrifuge capable of subjecting the samples to a g-force of about 350. One suitable centrifuge is a Heraeus LaboFuge 400 having a water collection basket, a digital rpm gauge, and a machined drainage basket adapted to hold and drain the bag samples. Where multiple samples are centrifuged, the samples must be placed in opposing positions within the centrifuge to balance the basket when spinning. The bags (including the wet, empty bags) are centrifuged at about 1,600 rpm (e.g., to achieve a target g-force of about 350), for 3 minutes. The bags are removed and weighed, with the empty bags (controls) being weighed first, followed by the bags containing the samples. The amount of solution retained by the sample, taking into account the solution retained by the bag itself, is the centrifuge retention capacity (CRC) of the sample, expressed as grams of fluid per gram of sample. More particularly, the retention capacity is determined as:

$$\frac{\text{sample/bag weight after centrifuge} - \text{empty bag weight after centrifuge} - \text{dry sample weight}}{\text{dry sample weight}}$$

The three samples are tested and the results are averaged to determine the retention capacity (CRC) of the superabsorbent material. The samples are tested at 23±1 degrees Celcius at 50±2 percent relative humidity.

Absorption Against Pressure (AAP) Test

The ability of a water-absorbing polymerizate to absorb liquid from a reservoir under a defined pressure (Absorption Against Pressure (AAP) (0.7 psi=49 g/cm$^2$)) is determined as follows: a 900 mg sample of the superabsorbent material is weighed in a plastic cylinder (inner diameter=6 cm, height=5 cm) having a screen fabric (mesh width=400 mesh) as bottom, dispersed uniformly, and weighted using a defined weight in the form of a plastic plate (diameter=5.98 cm), together with a metal piston (diameter=5.98 cm). The plastic plate is situated between the sample and the metal piston. Thereafter, the entire testing unit is placed on a glass filter plate (diameter=12 cm, porosity=0) which is covered with a filter paper and soaked with a 0.9% NaCl solution. The filter plate is embedded in the NaCl solution up to its top edge. The sample is allowed to absorb liquid for 60 minutes:

The plastic spacer and then the stainless steel weight are carefully placed into the cylinder. The weight of the completed AAP apparatus is recorded (A). The stainless steel weight is sized to exert a pressure load of about 49 g/cm$^2$. (It is noted that 49 g/cm$^2$=0.7 psi).

After 1 hour, the apparatus with the swollen sample is re-weighed, and the weight recorded (B). The gram amount of the NaCl solution that had been retained per gram of sample is calculated according to the following equation:

$$AAP=(B-A)/E$$

where AAP is in g/g at 0.7 psi. A is the weight in g of the AAP apparatus with the sample prior to absorbing the test solution. B is the weight in g of the AAP apparatus with the sample after absorbing the test solution for 1 hour and E is the dry weight in g of the sample.

Shear Modulus Test

Figure 8:
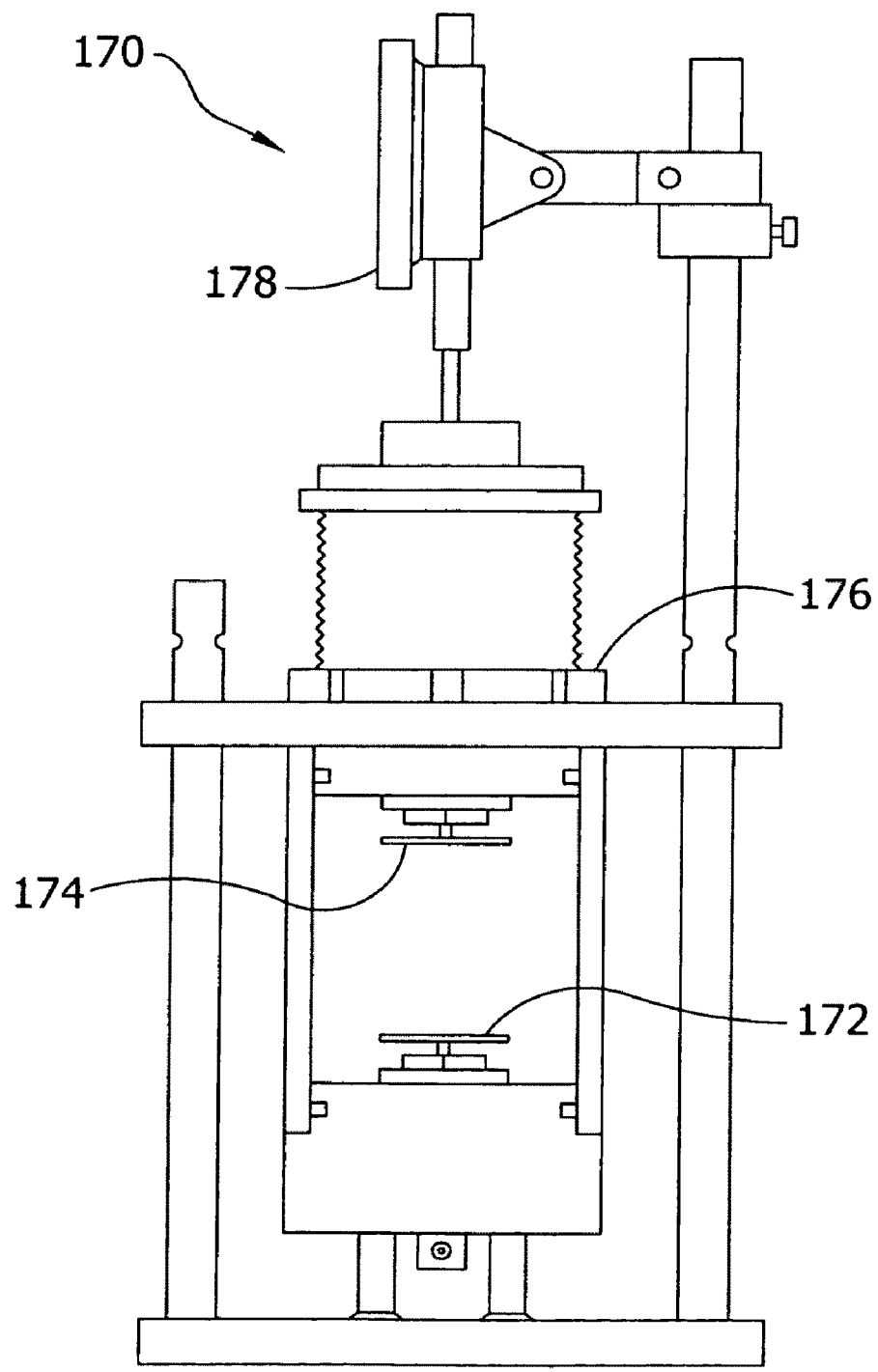
FIG. 8 is an elevation of apparatus for conducting a Shear Modulus Test.

The Shear Modulus Test measures the gel strength, or gel deformation tendency, of the superabsorbent material. The shear modulus is measured by a procedure that involves the use of a Rank Brothers Pulse Shearometer (FIG. 8) to measure the velocity of a torsional shear waver through the swollen superabsorbent material. This method avoids many of the problems associated with measuring the shear modulus of surface crosslinked superabsorbents using a traditional constant stress or constant strain rheometer or rheometers that rely on measuring the phase angle shift between stress and strain. The Shearometer, indicated generally in FIG. 8 at 170, comprises a circular lower plate, or disk 172 onto which a swollen sample of the superabsorbent material is placed. For this Test, reference is made to the operating manual "The Simple Solution to Shear Modulus Measurements" for the Rank Pulse Shearometer™. The instrument is constructed in such a way that a torsional shear wave can be propagated between a pair of parallel disks 172 and 174. Each disc is mounted on a piezoelectric transducer: one being used to initiate the shear wave, the other to detect the arrival of this wave a short time later. The separation of the disks can be varied by means of a screw adjustment 176 and then measured with a dial gauge 178. The propagation time of the shear wave is measured for each given disk separation. It is then possible to determine the wave velocity from the slope of a graph of propagation time plotted against disk separation. A value of shear modulus can then be calculated from the following approximation:

$$G=\rho V^2$$

wherein G is the shear modulus in NM$^{-2}$; $\rho$ is the density of the sample in kg.m$^{-3}$ and V is the wave propagation velocity in ms$^{-1}$.

The sample being tested is swollen to its gel volume in a synthetic urine. Excess free synthetic urine is removed from the sample by blotting on two paper towels for exactly one minute, strain.

The shear modulus (G') of the superabsorbent sample is calculated from the following formula:

$$G'=\text{Density}\times(\text{shear wave velocity})\times(\text{shear wave velocity}).$$

The elasticity of the sample may be related to the velocity of the wave in the following manner: For a passage of a shear wave through the sample, the storage component of the dynamic modulus (the elasticity), G', can be represented by the following equation:

$$G'=[V^2\rho(1-n^2)]/(1+n^2)^2$$

wherein V is the propagation velocity of light; $\rho$ is the density of the sample; and n is the ratio of the wavelength to the critical damping length. Measurements of the shear modulus can be obtained through consultancy groups such as the Bristol Colloid Center, University of Bristol, Bristol UK. In addition Rank Shearometers are offered on the Internet.

Preparation for performing the shear modulus test includes preparing synthetic urine which is made of 1% aqueous Triton X-100, 7.50 g; sodium chloride 30.00 g; anhydrous CaCl$_2$, 0.68 g; MgCl$_2$6H$_2$O 1.80 g; and DI water 3000.0 g.

About 90 g of synthetic urine are placed into 3 large beakers. Then an approximately 3.00 g sample of superabsorbent material is placed into each of three aluminum weighing pans. Each sample is added to a respective beaker of synthetic urine and timing begins. Each sample is allowed to swell to its equilibrium value, typically for 30 minutes. Each sample is stirred to ensure uniform liquid distribution. A large metal spatula is used to remove the hydrated samples from the beakers and spread evenly on 2 Wipe Alls L20 Kimtowels®, available from Kimberly-Clark, which are folded in half and stacked. The samples are blotted for exactly 60 seconds on the Wipe Alls. The spatula is used to spread the samples out over the paper toweling, only lightly pressing the samples onto the towel. No more force is applied than that required to distribute the sample. The sample is scraped up with the spatula and returned to the beakers after 60 seconds. The beakers are covered with foil or film until the samples are measured.

The shear moduli of the samples are measured within one hour of sample preparation. Each sample is transferred to a shearometer tube and placed on the lower disk 172, filling the shearometer tube to a height of at least 18 mm above the lower disk. The top disk 174 is lowered slowly until the top disk is exactly a distance of 12 mm from the bottom disk. The shear modulus G' is measured and recorded by measuring the time required for the torsional wave to pass through the sample at plate distances of 12 mm to 6 mm, measured at 1 mm decreasing increments. The slope of the linear time to disk separation distance plot provides the shear wave velocity used to calculate the shear modulus, G'.

In one embodiment, the superabsorbent material useful in making the absorbent structures of the present invention suitably has a retention capacity (CRC) as determined by the Centrifuge Retention Capacity Test described previously of at least 25 grams liquid per gram of superabsorbent material (g/g). In other embodiments, the superabsorbent material may have a retention capacity (CRC) as determined by the Centrifuge Retention Capacity Test of at least about 27.5 g/g and more suitably at least about 30 g/g.

The superabsorbent material also suitably has a free swell gel bed permeability (GBP) as determined by the Free Swell Gel Bed Permeability Test described previously of at least $350\times10^{-9}$ cm$^2$, more suitably at least about $400\times10^{-9}$ cm$^2$, and still more suitably at least about $500\times10^{-9}$ cm$^2$. In another embodiment, the free swell gel bed permeability of the superabsorbent material as determined by the Free Swell Gel Bed Permeability Test is suitably at least $575\times10^{-9}$ cm$^2$, more suitably at least about $600\times10^{-9}$ cm$^2$, more suitably at least about $700\times10^{-9}$ cm$^2$, yet more suitably at least about $800\times10^{-9}$ cm$^2$, still more suitably at least about $900\times10^{-9}$ cm$^2$ and even more suitably at least about $1,100\times10^{-9}$ cm$^2$.

The Absorbency Under Load value at 0.9 psi (also referred to as 0.9 AUL) of the superabsorbent material as determined by the AUL Test described previously is suitably at least 15 grams liquid per gram weight of superabsorbent material (g/g), more suitably at least about 18 g/g, still more suitably at least about 19 g/g and even more suitably at least about 20 g/g.

EXAMPLES

The following examples are provided to further illustrate the present invention and do not limit the scope of the claims. Unless otherwise stated all parts and percentages are by weight.

Example 1

In an insulated, flat-bottomed reaction vessel, 1866.7 g of 50% NaOH was added to 3090.26 g of distilled water and cooled to 25° C. 800 g of acrylic acid was then added to caustic solution and the solution again cooled to 25° C. A second solution of 1600 g of acrylic acid containing 9.6 g of polyethylene glycol (300) diacrylate was then added to the first solution, followed by cooling to 15° C., the addition of 9.6 g of monoallyl ether acrylate with 10 moles of ethoxylation, and additional cooling to 5° C., all while stirring. The monomer solution was then polymerized with a mixture of 100 ppm hydrogen peroxide, 200 ppm azo-bis-(2-amidino-propene)dihydrochloride, 200 ppm sodiumpersulfate and 40 ppm ascorbic acid (all aqueous solutions) under adiabatic conditions and held near $T_{max}$ for 25 minutes. The resulting gel was chopped and extruded with a Hobarth 4M6 commercial extruder, followed by drying in a Procter & Schwartz Model 062 forced air oven at 175° C. for 10 minutes with upflow and 6 minutes with downflow air on a 20 in×40 in perforated metal tray to a final product moisture level of less than 5 wt. %. The dried material was coarse ground in a Prodeva Model 315-S crusher, milled in an MPI 666-F three stage roller mill and sieved with an Minox MTS 600DS3V to remove particles greater than 850 microns and smaller than 150 microns. 400 g of the sieved powder was then blended uniformly with 0.2 wt. % kaolin (Neogen DGH), followed by the uniform spray application of a solution containing 0.5 wt. % aluminum sulfate, and 1.0 wt. % ethylene carbonate in 12 g of water, using a finely atomized spray while the SAP particles are fluidized in air. The coated material was then heated for 25 minutes at 186° C. in an electrically heated paddle drier.

Example 2

Similar to Example 1 except 12.0 g of polyethylene glycol (300) diacrylate and 12.0 g of monoallyl ether acrylate with 10 moles of ethoxylation were used in the monomer solution.

Example 3

In an insulated, flat-bottomed reaction vessel, 1866.7 g of 50% NaOH was added to 3090.26 g of distilled water and cooled to 25° C. 800 g of acrylic acid was then added to caustic solution and the solution again cooled to 25° C. A second solution of 1600 g of acrylic acid containing 120 g of 50 wt. % methoxypolyethyleneglycol(750) monomethacrylate in acrylic acid and 6.0 g of trimethylolpropanetriacrylate with 3 moles of ethoxylation were then added to the first solution, followed by cooling to 15° C., the addition of 10.8 g of allyl ether acrylate with 10 moles of ethoxylation, and additional cooling to 5° C., all while stirring. The monomer solution was then polymerized with a mixture of 100 ppm hydrogen peroxide, 125 ppm azo-bis-(2-amidino-propene) dihydrochloride, 300 ppm sodiumpersulfate and 30 ppm sodium erythorbate (all aqueous solutions) under adiabatic conditions and held near $T_{max}$ for 25 minutes. The resulting gel was chopped and extruded with a Hobarth 4M6 commercial extruder, followed by drying in a Procter & Schwartz Model 062 forced air oven at 175° C. for 10 minutes with upflow and 6 minutes with downflow air on a 20 in×40 in perforated metal tray to a final product moisture level of less than 5 wt. %. The dried material was coarse ground in a Prodeva Model 315-S crusher, milled in an MPI 666-F three stage roller mill and sieved with an Minox MTS 600DS3V to remove particles greater than 850 microns and smaller than 150 microns. 400 g of the sieved powder was then blended uniformly with 0.5 wt. % fumed alumina (Degussa Aluminumoxid C), followed by the uniform spray application of a solution containing 0.2 wt. % aluminum sulfate, 0.1 wt. % disodium cocoamphopropionate, 0.5 wt. % tetraethyleneglycol dimethyl ether, and 1.0 wt. % ethylene carbonate in 5 g of water, using a finely atomized spray while the SAP particles are fluidized in air. The coated material was then heated for 20 minutes at 180° C. in a General Signal/BM Model OV-510A-3 forced air oven.

Example 4

In an insulated, flat-bottomed reaction vessel, 1866.7 g of 50% NaOH was added to 3090.26 g of distilled water and cooled to 25° C. 800 g of acrylic acid was then added to caustic solution and the solution again cooled to 25° C. A second solution of 1600 g of acrylic acid containing 120 g of 50 wt. % methoxypolyethyleneglycol(750) monomethacrylate in acrylic acid and 14.4 g of trimethylolpropanetriacrylate with 3 moles of ethoxylation were then added to the first solution, followed by cooling to 15° C., the addition of 14.4 g of hydroxymonoallyl ether with 10 moles of ethoxylation, and additional cooling to 5° C., all while stirring. The monomer solution was then polymerized with a mixture of 100 ppm hydrogen peroxide, 200 ppm azo-bis-(2-amidino-propene) dihydrochloride, 200 ppm sodiumpersulfate and 40 ppm ascorbic acid (all aqueous solutions) under adiabatic conditions and held near $T_{max}$ for 25 minutes. The resulting gel was chopped and extruded with a Hobarth 4M6 commercial extruder, followed by drying in a Procter & Schwartz Model 062 forced air oven at 175° C. for 10 minutes with upflow and 6 minutes with downflow air on a 20 in×40 in perforated metal tray to a final product moisture level of less than 5 wt. %. The dried material was coarse ground in a Prodeva Model 315-S crusher, milled in an MPI 666-F three stage roller mill and sieved with an Minox MTS 600DS3V to remove particles greater than 850 microns and smaller than 150 microns. 400 g of the sieved powder was then blended uniformly with 0.5 wt. % fumed silica Aerosil 200 followed by the uniform spray application of a solution containing 0.01 wt. % aluminum sulfate and 1.0 wt. % ethylene carbonate in 4 g of water, using a finely atomized spray while the SAP particles are fluidized in air. The coated material was then heated for 135 minutes at 176° C. in an electrically heated paddle drier.

Experiment 1

Each of the superabsorbent materials set forth in Examples 1-4 were subjected to the Centrifuge Retention Capacity Test, the Free Swell Gel Bed Permeability Test, the Shear Modulus Test and the Absorption Against Pressure Test to determine liquid handling properties thereof. The results are set forth in Table 1 below.

TABLE 1

|  | CRC (g/g) | Free Swell GBP ($\times 10^{-9}$ cm$^2$) | G' (dynes/cm$^2$) | AAP (g/g) |
|---|---|---|---|---|
| Example 1 | 30 | 612 | 6899 | 21.2 |
| Example 2 | 29 | 862 | 7777 | 22.4 |
| Example 3 | 31 | 836 | 5182 | 19.7 |
| Example 4 | 27.8 | 1456 | 6872 | 20.8 |

For comparison purposes, various commercially available superabsorbent materials were also subjected to the Centrifuge Retention Capacity Test, the Free Swell Gel Bed Permeability Test, the Shear Modulus Test and the Absorption Against Pressure Test to determine liquid handling properties thereof. The results are set forth in Table 2 below.

TABLE 2

|  | CRC (g/g/) | G' (dynes/cm$^2$) | Free Swell GBP ($\times 10^{-9}$ cm$^2$) | AAP @0.7 psi (g/g) |
|---|---|---|---|---|
| Sanwet 770H | 32.4 | 4305 | 58 | 22.3 |
| Hy-Sorb M 7055 | 33.1 | 4276 | 55 | 24.2 |
| Hysorb 100 | 26.3 | 5649 | 95 | 24 |
| BASF 2300 | 33.4 | 4034 | 58 | 19.7 |
| BASF 7050 | 31.1 | 5033 | 62 | 26.5 |
| BASF 2260 | 23.9 | 9025 | 553 | 19.5 |
| BASF ASAP 2000 | 31.4 | 3688 | 50 | 21 |
| Sumitumo SA60 | 32.5 | 3196 | 37 | 13 |
| Kolon GS3400 | 30.4 | 6818 | 186 | 22.6 |
| Kolon GS3000 | 38.9 | 2811 | 20 | 22 |
| DryTech 2035M | 30.4 | 7138 | 35 | 15.1 |
| DOW S100R | 28.2 | 6032 | 88 | 24.3 |
| Aqualic CAB | 34.4 | 3356 | 176 | 17.4 |
| SAP from Pampers Baby Dry Diapers | 28.4 | 5746 | 143 | 20.6 |
| SAP from Pampers Premium diapers | 30.8 | 5573 | 130 | 23.3 |
| SAP from Pampers Cruisers | 28.9 | 6866 | 154 | 22.2 |
| SAP from Luv's diapers | 27.3 | 6954 | 137 | 22.0 |
| SAP from Huggies UltraTrim diaper | 21.5 | 11490 | 408 | 20.9 |
| SAP from Huggies Overnites | 29.6 | 6889 | 110 | 10.5 |
| SAP from Huggies Supremes | 22.2 | 11360 | 325 | 18.0 |
| SAP from White Cloud diaper | 22.1 | 9785 | 435 | 14.4 |
| SAP from White Cloud training pants | 22.3 | 9490 | 373 | 13.3 |
| SAP from Walgreens UltraValue diapers | 26.9 | 7590 | 278 | 15.9 |
| SAP from DriBottoms diapers | 22.4 | 9545 | 273 | 14.4 |
| SAP recovered from PaperPak Adult Briefs | 39.5 | 4554 | 10 | 13.1 |

Experiment 2

Various superabsorbent materials, set forth in Table 3 below, were subjected to the Free Swell Gel Bed Permeability Test, the Absorbency Under Load Test and the Centrifuge Retention Capacity Test to determine the liquid handling properties thereof. Superabsorbent materials A and B in Table 3 are conventional superabsorbent materials commercially available from Stockhausen, Inc. of Greensboro, N.C., U.S.A. as model designations SXM 880 and SXM 9543, respectively. Superabsorbent material C is a superabsorbent material reclaimed from a conventional diaper available from Procter & Gamble Co. of Cincinatti, Ohio, U.S.A, under the tradename Pampers Baby Dry. Superabsorbent materials D-M are superabsorbent materials made in accordance with the present invention by Stockhausen, Inc. of Greensboro, N.C., U.S.A. More particularly, superabsorbent materials D-I are experimental superabsorbent materials made by Stockhausen in accordance with the present invention and designated SP-1389 (Example 1 set forth above), SP-1390 (Example 2 set forth above), SP-1391, SP-1392, SP-1393 (Example 3 set forth above), and SP1394 (Example 4 set forth above), respectively. Superabsorbent materials J-M are additional experimental superabsorbent materials made by Stockhausen in accordance with the present invention and designated SP-1395, SP-1396, SR-1401 and SR-1402, respectively. The results are presented in Table 3 below.

TABLE 3

| Superabsorbent Material | CRC (g/g) | AUL (g/g) | | | | Free Swell GBP ($\times 10^{-9}$ cm$^2$) |
|---|---|---|---|---|---|---|
| | | At 0.01 psi | at 0.3 psi | at 0.6 psi | at 0.9 psi | |
| A | 29.9 | 46.9 | 31.8 | 26.8 | 23.4 | 60 |
| B | 23.3 | 35.2 | 26.2 | 23.0 | 20.6 | 300 |
| C | 29.4 | | | | 22.8 | 98 |
| D | 31.0 | 45.6 | 29.3 | 24.5 | 20.1 | 528 |
| E | 28.8 | 44.4 | 28.3 | 23.8 | 20.7 | 846 |
| F | 30.5 | 44.9 | 28.1 | 23.0 | 18.6 | 467 |
| G | 29.0 | 43.1 | 26.9 | 22.7 | 19.2 | 577 |
| H | 30.4 | 44.5 | 28.7 | 22.3 | 19.0 | 716 |
| I | 28.6 | 43.4 | 27.9 | 22.5 | 19.5 | 917 |
| J | 30.6 | 44.9 | 29.1 | 23.5 | 18.7 | 624 |
| K | 27.5 | 41.5 | 27.3 | 22.1 | 19.2 | 1140 |
| L | 31.6 | 46.9 | 26.2 | 20.6 | 15.6 | 485 |
| M | 27.3 | 44.2 | 27.6 | 23.0 | 18.5 | 1173 |

The absorbent structure of the present invention may be formed in any conventional manner, such as by being air-formed, air-laid, co-formed, bonded-carded or formed by other known techniques in which fibers and superabsorbent material are comingled to form a non-woven web. For example, the absorbent structure may alternatively be formed by in-situ polymerization, which typically involves first spraying a monomer onto the fibers and then polymerizing and crosslinking the monomer to form the superabsorbent material. As another alternative, the absorbent structure can be a laminate wherein the superabsorbent material is placed in a uniform or patterned array on at least one layer of permeable and hydrophilic fibers or web or between such layers.

The absorbent structure may be of substantially any shape and size suitable for its intended purpose. The absorbent structure may also comprise two or more non-woven webs or layers, which may be positioned in side-by-side relationship or surface-to-surface relationship, and all or a portion of adjacent webs or layers may be secured together to form the absorbent structure.

The superabsorbent material can be substantially homogeneously mixed with the hydrophilic fibers to provide a uniform distribution of the superabsorbent material and fibers throughout the absorbent structure. Alternatively, the superabsorbent material can be distributed non-uniformly within the absorbent structure, such as across the width, along the length and/or through the thickness of the structure to define discrete target regions or zones of the structure within which the superabsorbent material is distributed. The concentration of superabsorbent material within the absorbent structure can also be non-uniform through all or part of the thickness, across all or part of the width and/or along all or part of the length of the absorbent structure.

In general, the overall concentration of superabsorbent material within the absorbent structure is suitably about 90 weight percent or less based on the total weight of the absorbent structure, but is in any event greater than zero. In one embodiment, the concentration of superabsorbent material within the absorbent structure is suitably in the range of about 30 to about 90 weight percent, more suitably in the range of about 40 to about 90 weight percent and even more suitably in the range of about 40 to about 80 weight percent. In another embodiment the concentration of superabsorbent material within the absorbent structure is in the range of about 40 to about 60 weight percent.

The absorbent structure may or may not be wrapped or otherwise encompassed by a suitable tissue or web wrap for maintaining the integrity and/or shape of the absorbent structure.

Experiment 3

Six different absorbent structures (coded as structures 1-6 in Table 2 below) were made in a laboratory air-forming apparatus and subjected to various tests including a Saturation Capacity Test, an Absorbent Structure Permeability Test, a Fluid Intake Flowback Evaluation (FIFE) Test and a Vertical Wicking Test, all of which are described later herein, to assess the liquid handling properties of the absorbent structures. Each of the absorbent structures comprised a non-woven web of hydrophilic fibers (and more particularly hydrophilic fibers available from Weyerhauser of Federal Way, Wash., U.S.A. as model designation NB-416) and one of six different superabsorbent materials.

The first five absorbent structure codes reflect construction of the absorbent structure using superabsorbent materials described previously as being useful in making absorbent structures according to the present invention. More particularly, Code 1 corresponds to an absorbent structure incorporating superabsorbent material "E" from Table 3, Code 2 corresponds to an absorbent structure incorporating superabsorbent material "G" from Table 3, Code 3 corresponds to an absorbent structure incorporating superabsorbent material "I" from Table 3, Code 4 corresponds to an absorbent structure incorporating superabsorbent material "K" from Table 3 and Code 5 corresponds to an absorbent structure incorporating superabsorbent material "M" from Table 3. Code 6 corresponds to an absorbent structure incorporating the conventional superabsorbent material identified as superabsorbent material "B" in Table 3 and available from Stockhausen, Inc. as model designation SXM 9543.

For each absorbent structure code, three different type samples were produced for testing, designated in Table 4 below by the letters a, b and c. For "a" type samples the target superabsorbent concentration within the absorbent structure sample was about 45 percent and the target density was about 0.222 g/cm$^3$; for "b" type samples the target superabsorbent concentration was about 45 percent and the target density was about 0.353 g/cm$^3$; and for "c" type samples the target superabsorbent concentration was about 65 percent and the target density was about 0.353 g/cm$^3$. The target basis weight of each absorbent structure sample was approximately 600 grams per square meter (gsm).

The Saturation Capacity Test, Absorbent Structure Permeability Test, Fluid Intake Flowback Evaluation (FIFE) Test and Vertical Wicking Test were performed for each of the absorbent structure samples and the results are recorded in Table 4.

TABLE 4

| Code | Absorbent Structure Composition SAM type (from Table 3) | SAM (%) | Density g/cm³ | Sat. Cap. g/g | Absorbent Structure Permeability Free Swell ×10⁻⁸ cm² | at 0.3 psi ×10⁻⁸ cm² | Intake Rate (g/sec) @ 75 ml Load 1st Insult | 2nd Insult | 3rd Insult | 4th Insult | Vertical Wicking Capacity g |
|---|---|---|---|---|---|---|---|---|---|---|---|
| 1a | E | 45.0 | 0.222 | 18.0 | 24.2 | 17.6 | 1.81 | 1.01 | 2.81 | 2.48 | 103.7 |
| 2a | G | 45.0 | 0.222 | 17.2 | 32.7 | 23.5 | 2.05 | 1.06 | 2.82 | 2.30 | 102.4 |
| 3a | I | 45.0 | 0.222 | 18.0 | 39.4 | 26.3 | 2.12 | 1.01 | 2.64 | 2.34 | 106.5 |
| 4a | K | 45.0 | 0.222 | 18.4 | 32.7 | 21.9 | 2.11 | 1.02 | 2.84 | 2.53 | 105.8 |
| 5a | M | 45.0 | 0.222 | 19.1 | 25.9 | 12.4 | 1.97 | 1.02 | 2.40 | 2.05 | 114.3 |
| 6a | B | 45.0 | 0.222 | 15.6 | 25.0 | 17.1 | 1.87 | 1.02 | 1.68 | 1.47 | 93.4 |
| 1b | E | 45.0 | 0.353 | 17.2 | 23.1 | 11.6 | 1.42 | 1.01 | 2.58 | 2.29 | 120.8 |
| 2b | G | 45.0 | 0.353 | 17.5 | 25.3 | 17.9 | 1.56 | 1.03 | 2.10 | 1.76 | 123.9 |
| 3b | I | 45.0 | 0.353 | 18.1 | 41.0 | 16.9 | 1.44 | 1.02 | 2.27 | 1.96 | 107.7 |
| 4b | K | 45.0 | 0.353 | 17.3 | 29.3 | 23.8 | 1.62 | 1.01 | 2.47 | 2.07 | 108.0 |
| 5b | M | 45.0 | 0.353 | 18.3 | 14.8 | 15.4 | 1.51 | 1.02 | 1.74 | 1.53 | 121.6 |
| 6b | B | 45.0 | 0.353 | 14.9 | 21.9 | 9.4 | 1.28 | 1.01 | 1.17 | 0.95 | 96.7 |
| 1c | E | 65.0 | 0.353 | 22.7 | 22.3 | 8.9 | 1.35 | 1.01 | 1.79 | 1.64 | 110.8 |
| 2c | G | 65.0 | 0.353 | 22.0 | 18.2 | 8.3 | 1.35 | 1.01 | 1.88 | 1.74 | 122.0 |
| 3c | I | 65.0 | 0.353 | 21.7 | 22.8 | 9.7 | 1.46 | 1.01 | 2.27 | 2.00 | 118.1 |
| 4c | K | 65.0 | 0.353 | 21.5 | 24.2 | 9.6 | 1.39 | 1.01 | 1.78 | 1.53 | 121.8 |
| 5c | M | 65.0 | 0.353 | 22.8 | 14.4 | 5.7 | 1.29 | 1.01 | 1.43 | 1.34 | 118.9 |
| 6c | B | 65.0 | 0.353 | 17.3 | 14.6 | 8.9 | 1.18 | 1.02 | 1.53 | 1.43 | 94.8 |

In general, the absorbent structures made in accordance with the present invention (e.g., codes 1-5) exhibited enhanced liquid handling characteristics relative to the absorbent structure (code 6) incorporating the conventional superabsorbent material. For example, with respect to the intake rate as determined by the FIFE test, the absorbent structures made in accordance with the present invention generally exhibited greater intake rates than the absorbent structure incorporating the conventional superabsorbent material, particularly upon repeated insults of the absorbent structure (e.g., upon third and fourth insults thereof). The saturation capacity, absorbent structure permeability (both free swell and under 0.3 psi load) and wicking capacity of the absorbent structures made in accordance with the present invention were also generally better than those exhibited by the absorbent structure incorporating the conventional superabsorbent material.

Fluid Intake Flowback Evaluation Test

Figure 5:
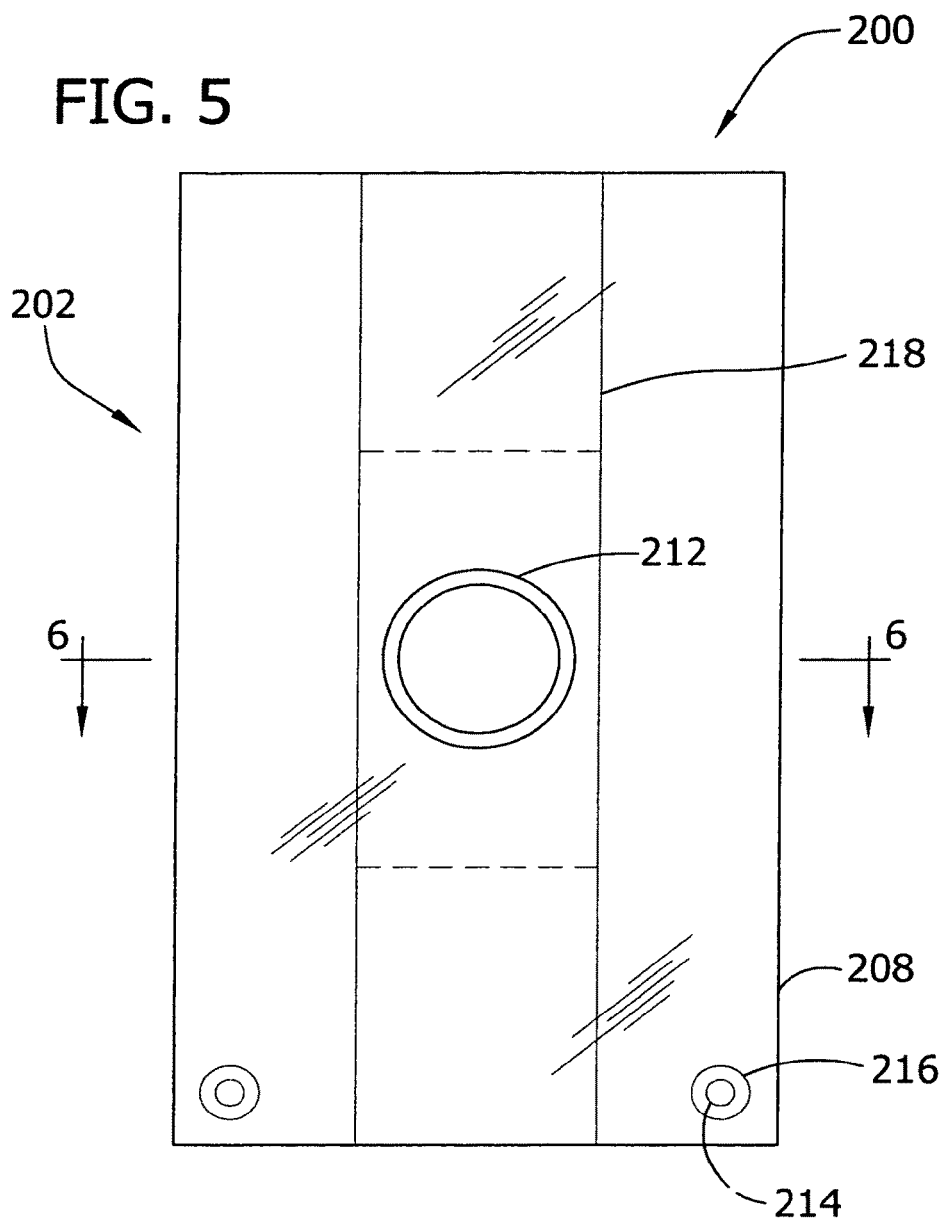
FIG. 5 is a top plan of apparatus for conducting a Fluid Intake Flowback Evaluation Test.
Figure 6:
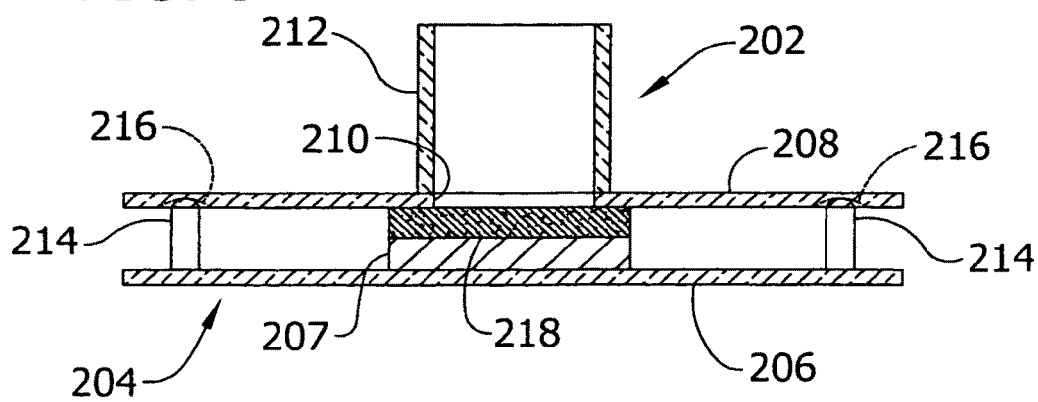
FIG. 6 is a section taken in the plane of line 6-6 of FIG. 5.

The Fluid Intake Flowback Evaluation (FIFE) Test determines the amount of time required for an absorbent structure, and more particularly a sample thereof, to take in (but not necessarily absorb) a known amount of test solution (0.9 weight percent solution of sodium chloride in distilled water at room temperature). A suitable apparatus for performing the FIFE Test is shown in FIGS. 5 and 6 and is generally indicated at 200. The test apparatus 200 comprises upper and lower assemblies, generally indicated at 202 and 204 respectively, wherein the lower assembly comprises a generally 14 inch (35.56 cm) by 8 inch (20.32 cm) rectangular plate 206 constructed of a transparent material such as Plexiglas and a generally 6 inch (15.24 cm) by 3 inch (7.62 cm) rectangular platform 207 centered on the plate for centering the absorbent structure sample during the test.

The upper assembly 202 comprises a generally rectangular plate 208 constructed similar to the lower plate 206 and having a central opening 210 formed therein. A cylinder 212 having an inner diameter of about 2 inches (about 5.08 cm) and a height of about 4 inches (about 10.16 cm) is secured to the upper plate 208 at the central opening 210 and extends upward substantially perpendicular to the upper plate. The central opening 210 of the upper plate 208 should have a diameter at least equal to the inner diameter of the cylinder 212 where the cylinder is mounted on top of the upper plate. However, the diameter of the central opening 210 may instead be sized large enough to receive the outer diameter of the cylinder 212 within the opening so that the cylinder is secured to the upper plate 208 within the central opening.

Pin elements 214 are located near outside corners of the lower plate 206, and corresponding recesses 216 in the upper plate 208 are sized to receive the pin elements to properly align and position the upper assembly 202 on the lower assembly during testing. The weight of the upper assembly 202 (e.g., the upper plate 208 and cylinder 212) is approximately 845 grams.

To run the FIFE Test, an absorbent structure sample 218 (either formed to the desire size or removed from an absorbent article and cut to the desired size) having length and width dimensions of about 14 inches (35.56 cm) by about 3 inches (7.68 cm) is weighed, with the tissue wrap on, and the weight is recorded in grams. The sample 218 is then centered on the platform 207 of the lower assembly. The upper assembly 202 is placed over the sample in opposed relationship with the lower assembly, with the pins 214 of the lower plate seated in the recesses 216 formed in the upper plate 208 and the cylinder 212 generally centered over the sample. Approximately 75 mL of the test solution (referred to herein as a first insult) is poured into the top of the cylinder 212 (e.g., generally at the height of the top of the cylinder) and allowed to flow down into the absorbent structure sample 218. A stopwatch is started when the first drop of solution contacts the sample 218 and is stopped when the liquid ring between the edge of the cylinder 212 and the sample disappears. The reading on the stopwatch is recorded to two decimal places and represents the intake time (in seconds) required for the first insult to be taken into the absorbent structure sample 218.

A time period of fifteen minutes is allowed to elapse, after which a second insult equal to the first insult is poured into the top of the cylinder 212 and again the intake time is measured as described above. The procedure is repeated for a third insult and then a fourth insult as well. An intake rate (in milliliters/second) for each of the four insults is determined by dividing the amount of solution (e.g., 75 mL) used for each insult by the intake time measured for the corresponding insult.

At least 3 samples of each absorbent structure are subjected to the FIFE Test and the results are averaged to determine the intake time and intake rate of the absorbent structure.

Absorbent Structure Permeability Test

The Absorbent Structure Permeability Test is used to determine the permeability of the absorbent structure, and more particularly a "z-direction" permeability of the absorbent structure based on liquid flow through the thickness of the structure. This test is substantially similar to the Free Swell Gel Bed Permeability Test set forth above, with the following noted exceptions. Referring back to FIGS. 1 and 2, instead of the cylinder height being about 5 cm, the cylinder height should be about 10 cm. Also, instead of particulate superabsorbent material being placed in the sample container, a circular absorbent structure sample 68 (e.g., either formed or otherwise cut from a larger absorbent structure), with any tissue wrap removed and having a cross-sectional diameter of about 6 cm is placed in the sample container 30 at the bottom of the cylinder 34 in contact with the screen 64. The sample container (without the piston and weight therein) is then submerged in a 0.9 weight percent saline solution for a time period of about 60 minutes to saturate the absorbent structure. The same height measurements obtained for the Free Swell Gel Bed Permeability Test are taken, e.g., with the container 30 empty and with the absorbent structure sample within the container and saturated.

The absorbent structure permeability measurement is initiated by delivering a continuous flow of saline solution into the sample container 30 with the saturated absorbent structure, the piston 36, and the weight 48 inside. The saline solution is delivered to the container 30 at a flow rate sufficient to maintain a fluid height of about 7.8 cm (instead of the 4 cm used for the Free Swell Gel Bed Permeability Test) above the bottom of the sample container. The quantity of fluid passing through the absorbent structure versus time is measured gravimetrically. Data points are collected every second for at least twenty seconds once the fluid level has been stabilized to and maintained at about 7.8 cm in height. The flow rate Q through the absorbent structure sample 68 is determined in units of grams/second (g/s) by a linear least-square fit of fluid passing through the container (in grams) versus time (in seconds). The permeability of the absorbent structure is then determined using the equation set forth above for the Free Swell Gel Bed Permeability Test.

Where the Absorbent Structure Permeability Test is conducted as described above, and more particularly where the absorbent structure sample is submerged in the solution without the piston and weight thereon, the test is said to be conducted under "free swell" conditions whereby the absorbent structure is allowed to swell free of any restraining load. In a variation of this test, the piston and weight may be placed on the sample within the container and then the entire assembly can be submerged so that a load (e.g., approximately 0.3 psi) is applied to the sample as the sample becomes saturated and swells. When conducted in this manner the test is referred to as being conducted "under load."

Vertical Wicking Test

The Vertical Wicking Test determines the amount of test solution (0.9 weight percent solution of sodium chloride in distilled water) that will wick upward into an absorbent structure during a 30 minute period.

A sample of the absorbent structure to be tested is prepared to have dimensions of about 3 inches wide by about 7 inches long, e.g., either formed or otherwise cut from a larger absorbent structure. The sample is then clamped to one face of an acrylic board measuring 25 cm high by 15 cm wide by 0.5 cm thick such that one end of the sample extends slightly beyond the bottom end of the acrylic board. The sample is further held in place on the board by two clamps extended around the side edges of the board so as to grasp the side edges of the sample near the top of the sample. The side of the board may be scaled in 1 mm increments to measure the vertical height of the wicked solution.

The sample (and board) is then hung from a free swinging support clamp and the sample is lowered into a reservoir of the test solution until the lower end of the sample contacts the solution. A timer with one second increments is started just as the sample contacts the liquid. The solution is allowed to be taken into the sample and wick upward therein for a period of about thirty minutes. The sample is then removed from the reservoir and taken off of the board and weighed. The difference between the weight of the sample after thirty minutes and the dry weight of the sample is the wicking capacity, in grams weight (g) of the absorbent structure.

Liquid Saturation Capacity Test

Figure 7:
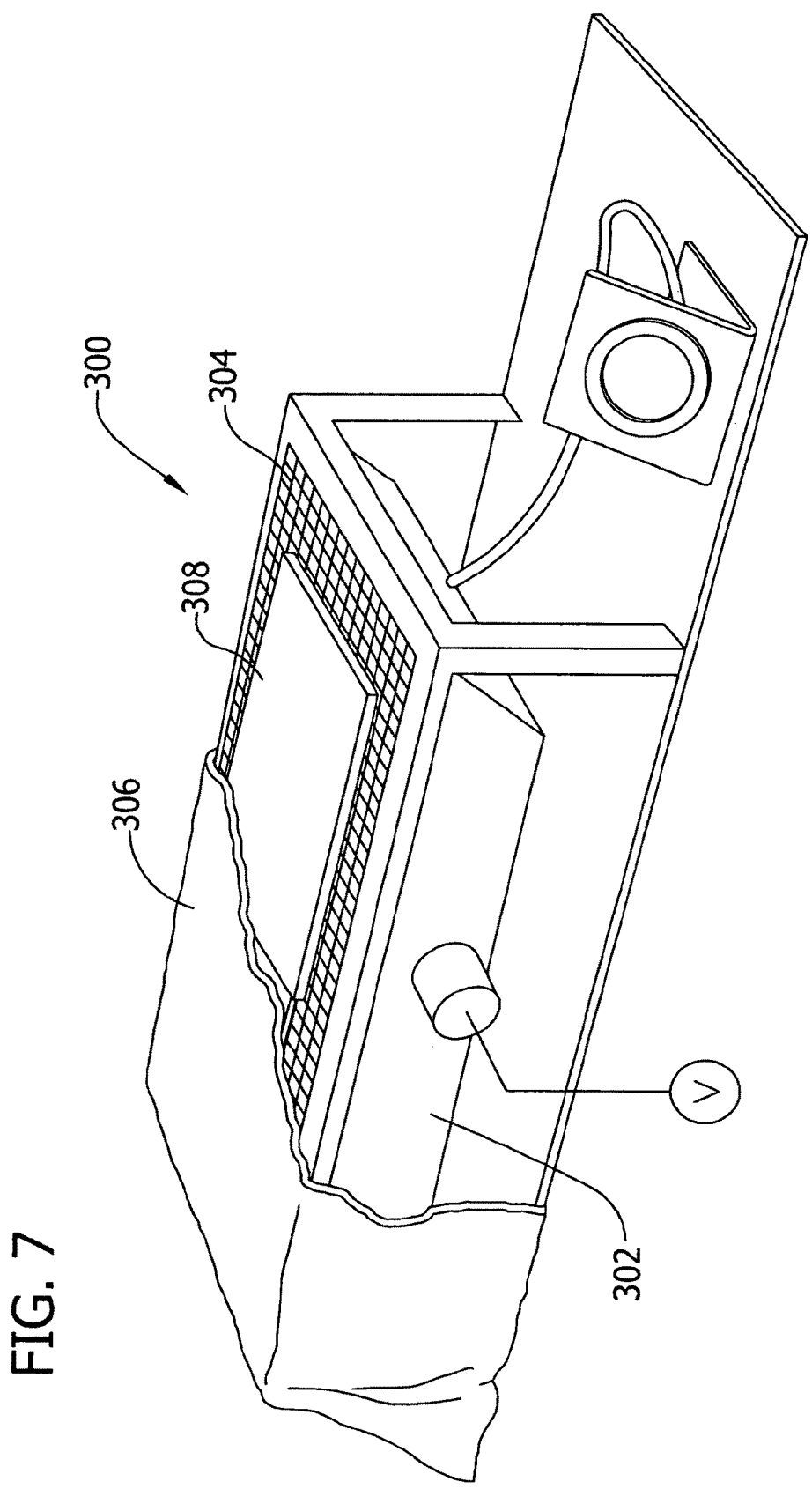
FIG. 7 is a cross-section of apparatus for conducting a Liquid Saturation Capacity Test.

The following test is used to determine a saturation capacity of an absorbent structure. With reference to FIG. 7, an absorbent structure sample 308 having length and width dimensions of approximately four inches by four inches (approximately 10.16 cm by 10.16 cm) is weighed with any tissue wrap material on and the weight in grams is recorded. The sample 308 is then wrapped in paper toweling (not shown), such as Scott paper towel available from Kimberly-Clark Worldwide Inc. of Neenah, Wis., U.S.A., and submerged in an excess quantity of 0.9 weight percent sodium chloride solution in distilled water at room temperature (e.g., about 23 degrees Celsius) for about twenty minutes. After this time period, the sample 308 is removed from the test solution and placed on a test apparatus, indicated generally at 300 in FIG. 7, comprising a vacuum box 302, a TEFLON fiberglass screen 304 having 0.25 inch (0.6 cm) openings and supported by the vacuum box, and a flexible rubber cover 306 sized for overlaying the screen on the vacuum box.

More particularly, the absorbent structure sample 308 (with toweling) is placed uncovered (by the rubber cover) on the screen 304 and allowed to drip dry for about one minute. The rubber cover 306 is then placed over the sample 308 and screen 304 (e.g., to generally form a seal over the vacuum box 302) and a vacuum (V) of about 0.5 pounds/square inch (about 34.5 dynes/square cm) is drawn on the vacuum box (and hence the sample) for a period of about five minutes. The sample 308 is then removed from the apparatus and the toweling is taken off the sample, making an effort to recover loose fibers and superabsorbent particles along with the sample. The recovered sample is again weighed and the weight in grams is recorded. The saturation capacity of the sample is determined by subtracting the dry weight of the sample from the weight of the recovered sample after application of the vacuum and then dividing by the dry weight of the sample and is recorded as grams of liquid retained per gram of absorbent structure (g/g).

If absorbent structure fibers and/or superabsorbent material are drawn through the fiberglass screen into the vacuum box during testing, a screen having smaller openings should be used and the test should be re-done. Alternatively, a piece of tea bag material or other similar material can be placed between the sample and the screen and the total retention capacity adjusted for the liquid retained by the tea bag or other material.

At least three samples of each absorbent structure are tested and the results are averaged to provide the retention capacity (e.g., total and normalized retention capacity) of the absorbent structure.

As described previously, the absorbent structure formed in accordance with the present invention may be incorporated in an absorbent article. As used herein, an absorbent article refers to an article which may be placed against or in proximity to the body of the wearer (e.g., contiguous to the body) to absorb and/or retain various waste discharged from the body. Some absorbent articles, such as disposable articles, are intended to be discarded after a limited period of use instead of being laundered or otherwise restored for reuse. In one embodiment, an absorbent article of the present invention comprises an outer cover, a bodyside liner positioned in facing relation with the outer cover and adapted for contiguous relationship with the body of the wearer, and an absorbent body disposed between the outer cover and the liner. The bodyside liner may be generally coextensive with the outer cover, or may instead overlie an area which is larger or smaller than the area of the outer cover, as desired.

In one embodiment, the outer cover is stretchable and may or may not be somewhat elastic. More particularly, the outer cover is sufficiently extensible such that once stretched under the weight of the insulted absorbent body, the outer cover will not retract substantially back toward its original position. However, it is contemplated that the outer cover may instead be generally non-extensible and remain within the scope of this invention.

The outer cover may be a single layer structure or it may be a multi-layered laminate structure to provide desired levels of extensibility as well as liquid impermeability and vapor permeability. For example, the outer cover can be a two-layer construction, including an outer layer constructed of a vapor permeable material and an inner layer constructed of a liquid impermeable material, with the two layers being secured together by a suitable laminate adhesive. The vapor permeable outer layer can be any suitable material and is desirably one which provides a generally cloth-like texture. Suitable materials for the outer layer include non-woven webs, woven materials and knitted materials. Non-woven fabrics or webs have been formed from many known processes, for example, bonded carded web processes, meltblowing processes and spunbonding processes.

The liquid impermeable inner layer of the outer cover can be either vapor permeable (i.e., "breathable") or vapor impermeable. The inner layer is desirably manufactured from a thin plastic film, although other flexible liquid impermeable materials may also be used. More particularly, the inner layer can be made from either cast or blown film equipment, can be coextruded and can be embossed if so desired. It is understood that the inner layer may otherwise be made from any suitable non-elastic polymer composition and may include multiple layers. Where the inner layer is vapor permeable, it may contain such fillers as micropore developing fillers, e.g. calcium carbonate; opacifying agents, e.g. titanium dioxide; and antiblock additives, e.g. diatomaceous earth. Suitable polymers for the inner layer include but are not limited to non-elastic extrudable polymers such as polyolefin or a blend of polyolefins, nylon, polyester and ethylene vinyl alcohol. More particularly, useful polyolefins include polypropylene and polyethylene. Other useful polymers include those described in U.S. Pat. No. 4,777,073 to Sheth, assigned to Exxon Chemical Patents Inc., such as a copolymer of polypropylene and low density polyethylene or linear low density polyethylene.

The bodyside liner is suitably pliable, soft feeling, and nonirritating to the wearer's skin, and is employed to help isolate the wearer's skin from the absorbent body. The liner is desirably less hydrophilic than the absorbent body to present a relatively dry surface to the wearer, and is sufficiently porous to be liquid permeable to thereby permit liquid to readily penetrate through its thickness. A suitable bodyside liner may be manufactured from a wide selection of web materials. Various woven and nonwoven fabrics including either or both synthetic and natural fibers can be used for the liner. For example, the bodyside liner may be composed of a meltblown or spunbonded web of the desired fibers, and may also be a bonded-carded-web. Layers of different materials that may have different fiber deniers can also be used. The various fabrics can be composed of natural fibers, synthetic fibers or combinations thereof.

The various components of the absorbent article are assembled together using a suitable form of attachment, such as adhesive, sonic bonds, thermal bonds or combinations thereof. For example, in one embodiment the outer cover and absorbent body are secured to each other with lines of adhesive, such as a hot melt or pressure-sensitive adhesive. The bodyside liner is also secured to the outer cover and may also be secured to the absorbent body using the same forms of attachment.

In accordance with the present invention, the absorbent body comprises at least in part an absorbent structure as described previously herein. It is contemplated that the absorbent body may comprise one or more of the absorbent structures, such as in overlaid or side-by-side relationship, and/or it may comprise one or more layers in addition to the absorbent structure, such as a surge layer, without departing from the scope of this invention.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description shall be interpreted as illustrative and not in a limiting sense.

What is claimed is:

1. An absorbent structure comprising at least in part a superabsorbent material comprising a crosslinked superabsorbent polymer or combination of polymers comprising from about 55 to about 99.9 weight percent of polymerizable unsaturated acid group containing monomers and ethylenically unsaturated monomers which can be copolymerized with the polymerizable unsaturated acid group containing monomers and which are selected from acrylamidopropyltrimethylammonium chloride and ethoxylated (meth)-acrylates, the superabsorbent material having a retention capacity (CRC) as determined by a Centrifuge Retention Capacity Test of at least about 25 g/g and a free swell gel bed permeability (GBP) as determined by a Free Swell Gel Bed Permeability Test of at least 575 $\times 10^{-9}$ cm$^2$, wherein the superabsorbent material in the absorbent structure comprises in the range of about 40 percent to about 60 percent of the weight of the absorbent structure.

2. An absorbent structure as set forth in claim 1 wherein the superabsorbent material has a free swell gel bed permeability as determined by the Free Swell Gel Bed Permeability Test of at least about 600 $\times 10^{-9}$ cm$^2$.

3. An absorbent structure as set forth in claim 1 wherein the superabsorbent material has a retention capacity as determined by the Centrifuge Retention Capacity Test of at least about 27.5 g/g.

4. An absorbent structure as set forth in claim 1 wherein the superabsorbent material has a retention capacity as determined by the Centrifuge Retention Capacity Test of at least about 30 g/g.

5. An absorbent structure as set forth in claim 1 wherein the superabsorbent material has an Absorbency Under Load (AUL) at 0.9 psi as determined by an Absorbency Under Load Test of at least about 15 g/g.

6. An absorbent structure as set forth in claim 1 further comprising at least one of hydrophilic fibers and hydrophobic fibers.

7. An absorbent structure as set forth in claim 6 wherein the hydrophilic fibers comprise cellulosic fibers.

8. An absorbent structure as set forth in claim 1 wherein the superabsorbent material comprises one of at least about 75 weight percent anionic polymer and at least about 75 weight percent cationic polymer.

9. An absorbent structure comprising at least in part a superabsorbent material comprising a crosslinked superabsorbent polymer or combination of polymers comprising from about 55 to about 99.9 weight percent of polymerizable unsaturated acid group containing monomers and ethylenically unsaturated monomers which can be copolymerized with the polymerizable unsaturated acid group containing monomers and which are selected from acrylamidopropyltrimethylammonium chloride and ethoxylated (meth)-acrylates, the superabsorbent material having a retention capacity (CRC) as determined by a Centrifuge Retention Capacity Test of at least about 25 g/g, an Absorbency Under Load (AUL) at 0.9 psi as determined by an Absorbency Under Load Test of at least about 18 g/g and a free swell gel bed permeability (GBP) as determined by a Free Swell Gel Bed Permeability Test of at least about 400$\times 10^{-9}$ cm$^2$, wherein the superabsorbent material in the absorbent structure comprises in the range of about 40 percent to about 60 percent of the weight of the absorbent structure.

10. An absorbent structure as set forth in claim 9 wherein the superabsorbent material has a free swell gel bed permeability as determined by the Free Swell Gel Bed Permeability Test of at least about 600$\times 10^{-9}$ cm$^2$.

11. An absorbent structure as set forth in claim 9 wherein the superabsorbent material has a retention capacity as determined by the Centrifuge Retention Capacity Test of at least about 27.5 g/g.

12. An absorbent structure as set forth in claim 11 wherein the superabsorbent material has a retention capacity as determined by the Centrifuge Retention Capacity Test of at least about 30 g/g.

13. An absorbent structure as set forth in claim 9 wherein the superabsorbent material has an Absorbency Under Load (AUL) at 0.9 psi as determined by the Absorbency Under Load Test of at least about 19 g/g.

14. An absorbent structure as set forth in claim 9 further comprising at least one of hydrophilic fibers and hydrophobic fibers.

15. An absorbent structure as set forth in claim 14 wherein the hydrophilic fibers comprise cellulosic fibers.

16. An absorbent structure as set forth in claim 9 wherein the superabsorbent material comprises one of at least about 75 weight percent anionic polymer and at least about 75 weight percent cationic polymer.

17. The absorbent structure as set forth in claim 1 wherein the superabsorbent material further comprises at least one of: from about 0.001 to about 5.0 weight percent of an internal crosslinking agent; from about 0.001 to about 5.0 weight percent of a surface crosslinking agent applied to the surface of the superabsorbent polymer; up to about 5 weight percent of a penetration modifier applied to the surface of the superabsorbent polymer; up to about 5 weight percent of a multivalent metal salt on the surface of the superabsorbent polymer; from about 0.01 to about 5 weight percent of a water-insoluble, inorganic powder; and up to about 5 weight percent of a surfactant on the surface of the superabsorbent polymer.

18. The absorbent structure as set forth in claim 1 wherein the superabsorbent material has a degree of neutralization of more than about 25 percent.

19. The absorbent structure as set forth in claim 9 wherein the superabsorbent polymer further comprises at least one of: from about 0.001 to about 5.0 weight percent of an internal crosslinking agent; from about 0.001 to about 5.0 weight percent of a surface crosslinking agent applied to the surface of the superabsorbent polymer; up to about 5 weight percent of a penetration modifier applied to the surface of the superabsorbent polymer; up to about 5 weight percent of a multivalent metal salt on the surface of the superabsorbent polymer; from about 0.01 to about 5 weight percent of a water-insoluble, inorganic powder; and up to about 5 weight percent of a surfactant on the surface of the superabsorbent polymer.

20. An absorbent structure comprising at least in part a superabsorbent material comprising a crosslinked superabsorbent polymer or combination of polymers comprising from about 55 to about 99.9 weight percent of polymerizable unsaturated acid group containing monomers and ethylenically unsaturated monomers which can be copolymerized with the polymerizable unsaturated acid group containing monomers and which are selected from acrylamidopropyltrimethylammonium chloride and ethoxylated (meth)-acrylates, the superabsorbent material having a retention capacity (CRC) as determined by a Centrifuge Retention Capacity Test of at least about 27.5 g/g, an Absorbency Under Load (AUL) at 0.9 psi as determined by an Absorbency Under Load Test of at least about 18 g/g and a free swell gel bed permeability (GBP) as determined by a Free Swell Gel Bed Permeability Test of at least about 350$\times 10^{-9}$ cm$^2$, wherein the superabsorbent material in the absorbent structure comprises in the range of about 40 percent to about 60 percent of the weight of the absorbent structure.

* * * * *

UNITED STATES PATENT AND TRADEMARK OFFICE
CERTIFICATE OF CORRECTION

PATENT NO.       : 8,021,998 B2                       Page 1 of 1
APPLICATION NO.  : 12/787914
DATED            : September 20, 2011
INVENTOR(S)      : Jian Qin et al.

It is certified that error appears in the above-identified patent and that said Letters Patent is hereby corrected as shown below:

In the Specification

In Column 8, Line 33, delete "polyethylene" and insert -- poly(ethylene -- therefor.

In Column 10, Line 33, delete "polyethylene" and insert -- poly(ethylene -- therefor.

In Column 11, Line 7, delete "shaft are" and insert -- shaft 38 are -- therefor.

Signed and Sealed this
Twelfth Day of May, 2015

Michelle K. Lee
*Director of the United States Patent and Trademark Office*